United States Patent
Strobel et al.

(10) Patent No.: US 7,105,513 B2
(45) Date of Patent: Sep. 12, 2006

(54) ACYLATED, HETEROARYL-CONDENSED CYCLOALKENYLAMINES AND THEIR USE AS PHARMACEUTICALS

(75) Inventors: Hartmut Strobel, Liederbach (DE); Paulus Wohlfart, Bensheim (DE)

(73) Assignee: Sanofi-Avertis Deutschland GmbH, Frankfurt (DE)

( * ) Notice: Subject to any disclaimer, the term of this patent is extended or adjusted under 35 U.S.C. 154(b) by 361 days.

(21) Appl. No.: 10/632,083

(22) Filed: Jul. 31, 2003

(65) Prior Publication Data

US 2004/0092513 A1 May 13, 2004

Related U.S. Application Data

(60) Provisional application No. 60/432,441, filed on Dec. 11, 2002.

(30) Foreign Application Priority Data

Aug. 7, 2002 (EP) ................... 02017586

(51) Int. Cl.
C07D 211/04 (2006.01)
C07D 333/78 (2006.01)
C07D 401/12 (2006.01)
C07D 401/14 (2006.01)
C07D 403/12 (2006.01)
C07D 417/12 (2006.01)
A61K 31/381 (2006.01)
A61K 31/435 (2006.01)
A61K 31/5377 (2006.01)

(52) U.S. Cl. ................. 514/233.5; 514/252.1; 514/299; 514/337; 514/365; 514/393; 514/406; 514/443; 544/131; 544/146; 544/405; 546/112; 546/279.1; 546/281.1; 548/200; 548/311.4; 548/364.4; 549/57

(58) Field of Classification Search ................ 544/131, 544/146, 405; 546/112, 279.1, 281.1; 548/200, 548/311.4, 364.4; 549/57; 514/233.5, 252.1, 514/299, 337, 365, 393, 406, 443
See application file for complete search history.

(56) References Cited

U.S. PATENT DOCUMENTS

| 5,075,303 | A | * | 12/1991 | Cliffe et al. ............. 514/218 |
|---|---|---|---|---|
| 5,527,815 | A | | 6/1996 | Tomiyama et al. |
| 5,753,662 | A | | 5/1998 | Peglion et al. |
| 6,048,880 | A | | 4/2000 | Kawai et al. |
| 6,258,829 | B1 | | 7/2001 | Takahashi et al. |
| 6,278,027 | B1 | | 8/2001 | Tomiyama et al. |
| 6,410,561 | B1 | | 6/2002 | Shinkai et al. |
| 6,617,359 | B1 | | 9/2003 | Strobel |
| 6,696,470 | B1 | | 2/2004 | Kawai et al. |
| 6,759,412 | B1 | | 7/2004 | Strobel |
| 6,812,253 | B1 | | 11/2004 | Strobel |
| 6,949,556 | B1 | | 9/2005 | Strobel |
| 2003/0022935 | A1 | | 1/2003 | Strobel |
| 2003/0055087 | A1 | | 3/2003 | Shinkai et al. |
| 2003/0055093 | A1 | | 3/2003 | Strobel |
| 2004/0082628 | A1 | | 4/2004 | Strobel |
| 2004/0110808 | A1 | | 6/2004 | Strobel |
| 2004/0142976 | A1 | | 7/2004 | Kawai et al. |
| 2004/0225013 | A1 | | 11/2004 | Strobel |
| 2005/0054729 | A1 | | 3/2005 | Strobel |
| 2005/0101599 | A1 | | 5/2005 | Zeiher |

FOREIGN PATENT DOCUMENTS

| CA | 2151443 | 9/1995 |
|---|---|---|
| JP | 02-255664 | 10/1990 |
| JP | 08-325234 | 12/1996 |
| WO | WO 99/47153 | 9/1999 |
| WO | WO 00/03746 | 1/2000 |
| WO | WO 01/68652 | 9/2001 |

OTHER PUBLICATIONS

Duda et al.I, Trends in Molecular Medicine, 10(4), 143-145, Apr. 2004.*
Endres et al, Trends in Neurosciences, 27(5), 283-289, May 2004.*
Li et al, Nitric Oxide, 7, 149-164, 2002.*
Sase et al, Trends in Cardiovascular Medicine, 7(1), 28-37, Jan. 1997.*
Bianchi, et al., Regioselectivity in the Reactions of Benzonitrite N-Phenyl-Imide and Some Benzonitrite N-Oxides with a,B-Unsaturated Ketones., J. Chem. Res, Synop. (1981) 6-7.
Binder, et al., A Facile Route to Functionalized Cyclopenta [b] thiophenones Based on the Structure of the Selective COX-2 Inhibitor Flosulide, Monatsh. Chem 129, (1998), 887-896.
Caprathe, et al., Dopamine Autoreceptor Agonists as Potential Antipsychotics. 3. 1 6-Propyl-4,5,5a,6,7,8-hexahydrothiazolo [4,5-f] quinolin-2-amine, J. Med. Chem. 34, (1991), 2736-2746.
Dammertz, et al., Synthase Von 6,7,8,9-Tetrahydro-5H-cyclohepta[b] pyridin-5-on, Arch. Pharm. 310 (1977), 172-176.
Endres, et al. , Stroke Protection By 3-Hydroxy-3-Methylglutaryl (HMG)—CoA Reductase Inhibitors Medicated By Endothelial Nitric Oxide Synthase, Proc. Natl. Acad. Sci. USA, 95 (1998) 8880-8885.

(Continued)

Primary Examiner—Fiona T. Powers
(74) Attorney, Agent, or Firm—Jiang Lin; Paul Darkes

(57) ABSTRACT

The present invention relates to acylated, heteroaryl-condensed cycloalkenylamines, to pharmaceutical compositions comprising such compounds, to methods for the stimulation of the expression of endothelial NO synthase, and methods of treatment comprising administering such compounds.

9 Claims, No Drawings

OTHER PUBLICATIONS

Hicks, et al., The Synthesis And Photochemical Behaviour Of Some Annelated Tropones, J. Chem. Soc. Perkin Trans. 1, (1984) 2297-2304.

Hoffman, et al., Synthesis Of 3-Nitro-5-Acylpyridines By Condensation Of Sodium Nitromalonaldehyde/Tosyl Chloride With 2-Amino-1-Acyl Olefins. Evidence For the Intermediacy of 3-Chloro-2-Nitroacrolein, J. Org. Chem. 49 (1984), 193-195.

Huang, et al., The Improved Preparation Of 7,8-Dihydro-Quinoline-5(6H)-One and 6,7-Dihydro-5H-1-Pyrindin-5-One, Synth. Commun. 28 (1998), 1197-1200.

Jones, et al., Synthesis Of 4-H-Cyclohepta [b] thiophen-4-ones, 4H-Cyclohepta [b] furna-4-one, and 9H-Cyclohepta[b] pyridin-9-one, J. Chem. Soc., Perkin Trans., 1, (1973), 968-972.

Koehler, et al., Potential Anticancer Agents IX. Tetrahydroquinazoline Analogs Of Tetrahydrofolic Acid. I, J. Am. Chem. Soc. 80 (1958) 5779-5785.

Li, et al., Activation Of Protein Kinase Ca and/or e Enhances Transcription of the Human Endothelial Nitric Oxide Synthase Gene, Mol. Pharmacol. 53 (1998) 630-637.

MacDowell, et al., The Use Of 2,5-Dichlorothiophene in The Synthesis Of 3,4-Disubstituted Thiophenes, J. Org. Chem. 32 (1967) 1226-1229.

Moroi, et al., Interaction of Genetic Deficiency of Endothelial Nitric Oxide, Gender, and Pregnancy in Vascular Response to Injury in Mice, J. Clin. Invest., 101 (1998) 1225-1232.

Muraro, et al., Heterocycles sulfures condenses.—Synthese et dechloration de dichloro-1,3 thieno (c) cyclenones,, Bull. Soc. Chim. Fr., Pt. 2, (1973) 335-342.

Muraro, et al., Recherches dans le domaine des thieno (c) cyclenones., C.R. Acad. Sci., Ser. C, 273 (1971) 1362-1367.

Nakayama, et al., T- 786—C Mutation in the 5'-Flanking Region of the Endothelial Nitric Oxide Synthase Gene Is Associated With Coronary Spasm, Circulation 99 (1999) 2864-2870.

Nayyar, et al., New Approach for the General Synthesis of Oxotetrahydroindoles via Intramolecular Cycloadditions of Azomethine Ylides with Tethered Alkynes, J. Org. Chem. 62 (1997) 982-991.

Ravina, et al., Conformationally Constrained Butyrophenones with Mixed Dopaminergic (D2) and Serotoninergic (5-HT2A, 5-HT2C) Affinities: Synthesis, Pharmacology, 3D-QSAR, and Molecular Modeling of (Aminoalkyl) benzo- and—thienocycloalkanones as Putative Atypical Antipsychotics, J. Med. Chem. 42 (1999) 2774-2797.

Reimann, et al., Regioselektive Synthase von 4-Methyl-1-pyridin-5-on, Pharmazie 50 (1995) 589-592.

Ruangsiyanand, et al., Enamine Cyclischer 1.3-Diketone als Ausgangsstoffe fur Pyridinringsynthesen, Chem. Ber. 103 (1970) 2403-2410.

Schenone, et al., Reaction of 2-Dimethylaminomethylene-1,3-diones with Dinucleophiles. I. Synthesis of 1,5-Disubstituted 4-Acylpyrazoles, J. Heterocyclic Chem., 19 (1982) 1355-1361.

Schroeder, et al., Nichtsteroldale Entzundungshemmer. 3. Substituierte Aza-Tetralin—und Aza-indancarbonsauren Mit Antiphlogistischer Wirkung, J. Med. Chem.—Chim. Ther. 14 (1979) 309-315.

Sessa, et al., Chronic Exercise In Dogs Increases Coronary Vascular Nitric Oxide Production And Endothelial Cell Nitric Oxide Synthase Gene Expression, Circ. Research 74 (1994) 349-353.

Shigeki, et al., 7-Oxocyclopenta[d]Pyrimidine Derivative, esp@cenet database—12 -Document Bibliography and Abstract, no date available.

Takeshi, et al., Benzoic Acid Derivative Or Its Salt, esp@cenet database -12—Document Bibliography and Abstract, no date available.

Varenne, et al., Percutaneous Gene Therapy Using Recombinant Adenoviruses Encoding Human Herpes Simplex Virus Thymidine Kinase, Human PAI-1, and Human NOS3 in Balloon-Injured Porcine Coronary Arteries, Hum. Gene Ther. 11 (2000) 1329-1339.

Westerwelle, et al., B-Aminoketone als Schlusselverbindungen zur Synthase von Pyridinen: Eln Neuartiger, Leistungsfahiger Zugang zu Kondensierten Bi- und Terpyridinen, Chem. Ber. 124 (1991) 571-576.

* cited by examiner

ACYLATED, HETEROARYL-CONDENSED CYCLOALKENYLAMINES AND THEIR USE AS PHARMACEUTICALS

This application is entitled to the benefit of earlier filed U.S. Provisional Application No. 60/432,441, filed Dec. 11, 2002. The content of U.S. Provisional Application 60/432,441 is incorporated herein by reference.

The present invention relates to acylated, heteroaryl-condensed cycloalkenylamines of the formula I,

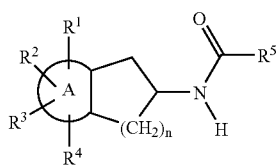

in which A, $R^1$, $R^2$, $R^3$, $R^4$, $R^5$ and n have the meanings indicated below. The compounds of formula I are valuable pharmaceutically active compounds which are useful in the treatment of various disease states including cardiovascular disorders such as atherosclerosis, thrombosis, coronary artery disease, hypertension and cardiac insufficiency. They upregulate the expression of the enzyme endothelial nitric oxide (NO) synthase and can be applied in conditions in which an increased expression of said enzyme or an increased NO level or the normalization of a decreased NO level is desired. The invention furthermore relates to processes for the preparation of compounds of the formula I, their use, in particular as active ingredients in pharmaceuticals, pharmaceutical preparations comprising them, methods of stimulating the expression of endothelial NO synthase, and methods of treatment comprising administering such compounds.

Endothelial NO synthase (eNOS, NOS-III) belongs to a group of three isoenzymes which produce nitric oxide (NO) by oxidation of arginine. Endothelially released NO is of central importance in a number of key cardiovascular mechanisms. It has a vasodilating effect and inhibits the aggregation of platelets, the adhesion of leukocytes to the endothelium and the proliferation of intimal smooth muscle cells.

Endothelial NO synthase is subject to physiological and pathophysiological regulation both at the transcriptional and at the post-transcriptional level. Enzyme already present in the endothelium may undergo calcium-dependent and calcium-independent activation through phosphorylation of specific amino acids, but also by direct interactions with specific proteins. Stimulators of this, usually transient, NO release are, extracellular arginine, 17β-estrogen and the mechanical stimulus exerted on the luminal surface of the endothelium by the blood flow (shear stress). The latter additionally leads to regulation of eNOS at the transcriptional level. Thus, for example, Sessa et al. (Circ. Research 74 (1994) 349, the content of which is incorporated herein by reference) were able by means of exercise training and the increase in shear stress associated therewith to obtain a marked increase in eNOS.

Whether regulation at the post-transcriptional level is relevant in vivo, has not been unambiguously proven. Thus, for example, administration of a high arginine dose is followed by only a transient improvement in the endothelium-dependent vasorelaxation in patients with coronary heart disease.

On the other hand, the significance of the upregulation of the eNOS protein is scientifically accepted. Thus, there are findings which show that the protective properties of the HMG-CoA reductase inhibitor simvastatin can be attributed, besides to the lipid lowering effect, also in part to an increase in eNOS expression in vivo (Endres et al., Proc. Natl. Acad. Sci. USA 95 (1998) 8880, the content of which is incorporated herein by reference). It is additionally known that single point mutations in the 5'-flanking region of the eNOS gene ("eNOS promoter"), and the reduction in the rate of eNOS gene transcription associated therewith, in the Japanese population is associated with an increase in the risk of coronary spasms (Nakayama et al., Circulation 99 (1999) 2864, the content of which is incorporated herein by reference).

The current assumption therefore is that the transcriptional and post-transcriptional mechanisms of eNOS regulation are seriously disturbed in a large number of disorders, especially in cardiovascular disorders. Even in very early stages of a wide variety of cardiovascular disorders it is possible for a dysfunction of this type in the endothelium lining the blood vessels to lead to a deficiency of bioactive NO, which is manifested as the disorder progresses in the form of measurable pathophysiological and morphological changes. Thus, critical steps in early atherogenesis are speeded up by a decrease in endothelial NO release, such as, for example, the oxidation of low density lipoproteins, the recruitment and deposition of monocytes in the intima of vessels, and the proliferation of intimal cells. A consequence of atherogenesis is the formation of plaques on the inside of the blood vessels, which may in turn lead, through a diminution in the shear stress, to a further decrease in endothelial NO release and a further deterioration in the pathology. Since endothelial NO is also a vasodilator, a decrease thereof frequently also leads to hypertension, which may, as an independent risk factor, cause further organ damage.

The aim of a therapeutic approach to the treatment of these disorders must accordingly be to interrupt this chain of events by increasing the endothelial NO expression. Gene transfer experiments which lead in vitro to overexpression of NO synthase in previously damaged vessels are in fact able to counteract the described processes and are thus evidence of the correctness of this approach (Varenne et al., Hum. Gene Ther. 11 (2000) 1329, the content of which is incorporated herein by reference).

Some low molecular weight compounds which, in cell cultures, may lead to a direct effect on eNOS transcription and expression are disclosed in the literature. The statins which have already been mentioned are, however, the only substances for which it has been possible to date to show such an increase in eNOS in vivo as a side effect. But in view of the known range of side effects of this class of substances it is unclear how far this effect is present in a toxicologically unproblematic dose.

Liao et al. claim in WO 99/47153 and WO 00/03746 (the content of each of which is incorporated herein by reference) the use of rhoGTPase inhibitors and agents which influence the organization of the actin cytoskeleton for increasing eNOS in endothelial cells and for the therapy of various disorders such as, for example, stroke or pulmonary hypertension without, however, indicating a specific way of achieving this.

WO 02/064146, WO 02/064545, WO 02/064565 and WO 02/064546 (the content of each of which is incorporated herein by reference) disclose acylated, benzo-condensed cycloalkenylamines which upregulate eNOS expression in endothelial cells and are useful pharmaceutically active ingredients for the treatment of various diseases, but there is an ongoing need for further eNOS expression enhancers with a favorable property profile. The present invention satisfies this need by providing the compounds of the formula I and methods of using them.

Certain acylated cycloalkenylamines condensed to an imidazole ring which bind to the histamine H3 receptor and are useful, for example, for the treatment of overweight and obesity, are disclosed in WO 01/68652 (the content of which is incorporated herein by reference). JP 08/325234 (the content of which is incorporated herein by reference) discloses cycloalkenylamines condensed to an imidazole ring which carry a 2-alkoxy-4-amino-5-halobenzoyl substituent on the amino group and are 5-HT-4 receptor agonists useful, for example, for the treatment of schizophrenia. EP 1072263 (the content of which is incorporated by reference) discloses nociceptin antagonists useful as analgesics which include certain acylamino-substituted 5,6,7,8-tetrahydroquinoline derivatives. N-(2-amino-5,6,7,8-tetrahydro-4-hydroxyquinazolin-6-yl)-3,4-dichlorobenzamide has been described by Koehler et al. in J. Am. Chem. Soc. 80, 5779 (1958), the content of which is incorporated herein by reference.

A subject of the present invention are acylated, heteroaryl-condensed cycloalkenylamines of the formula I,

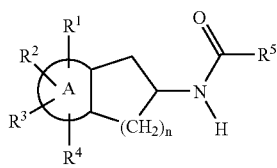

I in any of their stereoisomeric forms and mixtures thereof in any ratio, and the pharmaceutically acceptable salts thereof, wherein in the formula I:

the ring A, which comprises the two carbon atoms common to the ring A and the cycloalkenyl ring in formula I, is an aromatic 5-membered or 6-membered ring containing 1 or 2 nitrogen atoms as ring heteroatoms, or an aromatic 5-membered ring containing 1 ring heteroatom which is an oxygen atom or a sulfur atom or 2 ring heteroatoms one of which is a nitrogen atom and the other of which is an oxygen atom or a sulfur atom;

$R^1$ and $R^4$ are independently from each other selected from the group consisting of: H; unsubstituted and at least monosubstituted $C_1$–$C_{10}$-alkyl, $C_2$–$C_{10}$-alkenyl and $C_2$–$C_{10}$-alkynyl, the substituents of which are selected from the group consisting of F, OH, $C_1$–$C_8$-alkoxy, $C_1$–$C_8$-alkylmercapto, —CN, $COOR^6$, $CONR^7R^8$, and unsubstituted and at least monosubstituted phenyl and heteroaryl where the substituents of the phenyl and heteroaryl groups are selected from the group consisting of halogen, —CN, $C_1$–$C_3$-alkyl, $C_1$–$C_3$-alkoxy and $CF_3$; unsubstituted and at least monosubstituted phenyl and heteroaryl the substituents of which are selected from the group consisting of halogen, —CN, $C_1$–$C_3$-alkyl, $C_1$–$C_3$-alkoxy and $CF_3$; $COR^9$; $CONR^{10}R^{11}$; $COOR^{12}$; $CF_3$; halogen; —CN; $NR^{13}R^{14}$; $OR^{15}$; $S(O)_mR^{16}$; $SO_2NR^{17}R^{18}$; and $NO_2$; but cannot be halogen, —CN or $NO_2$ if $R^1$ or $R^4$ is bonded to a ring nitrogen atom;

$R^2$ and $R^3$ are independently from each other selected from the group consisting of: H; halogen; unsubstituted and at least monosubstituted $C_1$–$C_{10}$-alkyl the substituents of which are selected from the group consisting of OH, phenyl, and heteroaryl; OH; $C_1$–$C_{10}$-alkoxy; phenoxy; $S(O)_mR^{19}$; $CF_3$; —CN; $NO_2$; $C_1$–$C_{10}$-alkylamino; di($C_1$–$C_{10}$-alkyl) amino; ($C_1$–$C_6$-alkyl)—CONH—; unsubstituted and at least monosubstituted phenyl-CONH— and phenyl-$SO_2$—O— the substituents of which are selected from the group consisting of halogen, —CN, methyl and methoxy; $C_1$–$C_6$-alkyl-$SO_2$—O—; unsubstituted and at least monosubstituted ($C_1$–$C_6$-alkyl)—CO— the substituents of which are selected from the group consisting of F, di($C_1$–$C_3$-alkyl)amino, pyrrolidinyl and piperidinyl; and phenyl-CO— the phenyl part of which is unsubstituted or at least monosubstituted by substituents selected from the group consisting of $C_1$–$C_3$-alkyl, halogen and methoxy; but cannot be halogen, —CN or $NO_2$ if $R^2$ or $R^3$ is bonded to a ring nitrogen atom;

where, if A is a 6-membered aromatic ring, 2 or 3 of the groups $R^1$, $R^2$, $R^3$ and $R^4$ are present and are bonded to the carbon atoms in the ring A which are not shared with the cycloalkenyl ring, and, if A is a 5-membered aromatic ring, 1, 2 or 3 of the groups $R^1$, $R^2$, $R^3$ and $R^4$ are present and are bonded to the carbon atoms in the ring A which are not shared with the cycloalkenyl ring and, in the case of a pyrrole, pyrazole or imidazole ring, to 1 ring nitrogen atom;

$R^5$ is a group Ar or a group Hetar both of which are unsubstituted or carry one or more identical or different substituents selected from the group consisting of: halogen; —CN; $NH_2$; unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, $C_1$–$C_{10}$-alkylamino and di($C_1$–$C_{10}$-alkyl)amino, the substituents of which are selected from the group consisting of F, OH, $C_1$–$C_8$-alkoxy, aryloxy, $C_1$–$C_8$-alkylmercapto, $NH_2$, $C_1$–$C_8$-alkylamino and di($C_1$–$C_8$-alkyl)amino; $C_3$–$C_5$-alkandiyl; phenyl; heteroaryl; aryl-substituted or heteroaryl-substituted $C_1$–$C_4$-alkyl; $CF_3$; $NO_2$; OH; phenoxy; benzyloxy; ($C_1$–$C_{10}$-alkyl)—COO—; $S(O)_mR^{20}$; SH; phenylamino; benzylamino; ($C_1$–$C_{10}$-alkyl)—CONH—; ($C_1$–$C_{10}$-alkyl)—CO—N($C_1$–$C_4$-alkyl)—; phenyl-CONH—; phenyl-CO—N($C_1$–$C_4$-alkyl)—; heteroaryl-CONH—; heteroaryl-CO—N($C_1$–$C_4$-alkyl)—; ($C_1$–$C_{10}$-alkyl)—CO—; phenyl-CO—; heteroaryl-CO—; $CF_3$—CO—; —$OCH_2O$—; —$OCF_2O$—; —$OCH_2CH_2O$—; —$CH_2CH_2O$—; $COOR^{21}$; $CONR^{22}R^{23}$; C(NH)—$NH_2$; $SO_2NR^{24}R^{25}$; $R^{26}SO_2NH$—; $R^{27}SO_2N(C_1$–$C_6$-alkyl)—; and a residue of a saturated or at least monounsaturated aliphatic, monocyclic 5-membered to 7-membered heterocycle containing 1, 2 or 3 heteroatoms selected from the group consisting of N, O and S, which heterocycle can be substituted by one or more substituents selected from the group consisting of halogen, $C_1$–$C_3$-alkyl, $C_1$–$C_3$-alkoxy, OH, oxo and $CF_3$, where said heterocycle can optionally be condensed to the said group Ar or the said group Hetar; wherein all aryl, heteroaryl, phenyl, aryl-containing, heteroaryl-containing and phenyl-containing groups, which are optionally present in the said substituents of the said group Ar or the said group Hetar, can be substituted by one or more substituents selected from the group consisting of halogen, —CN, $CF_1$–$C_3$-alkyl, OH, $C_1$–$C_3$-alkoxy, and $CF_3$;

$R^6$ is selected from the group consisting of:

H; $C_1$–$C_{10}$-alkyl which can be substituted by one or more substituents selected from the group consisting of F, $C_1$–$C_8$-alkoxy and di($C_1$–$C_8$-alkyl)amino; aryl-($C_1$–$C_4$-alkyl)— and heteroaryl-($C_1$–$C_4$-alkyl)— both of which can be substituted by one or more substituents selected from the group consisting of halogen, $C_1$–$C_4$-alkyl, $C_1$–$C_4$-alkoxy and di($C_1$–$C_6$-alkyl)amino;

$R^7$ is selected from the group consisting of:
H; $C_1$–$C_{10}$-alkyl which can be substituted by one or more substituents selected from the group consisting of F, $C_1$–$C_8$-alkoxy, di($C_1$–$C_8$-alkyl)amino and phenyl; phenyl; indanyl; and heteroaryl; wherein each of the aromatic groups can be unsubstituted or carry one or more substituents selected from the group consisting of halogen, —CN, $C_1$–$C_3$-alkyl, $C_1$–$C_3$-alkoxy and $CF_3$;

$R^8$ is H or $C_1$–$C_{10}$-alkyl;

$R^9$ is selected from the group consisting of:
$C_1$–$C_{10}$-alkyl which can be substituted by one or more substituents from the group consisting of F, $C_1$–$C_4$-alkoxy and di($C_1$–$C_3$-alkyl)amino; and unsubstituted and at least monosubstituted phenyl and heteroaryl the substituents of which are selected from the group consisting of $C_1$–$C_3$-alkyl, $C_1$–$C_3$-alkoxy, halogen, —CN and $CF_3$;

$R^{10}$, independently from $R^7$, is defined as $R^7$;
$R^{11}$, independently from $R^8$, is defined as $R^8$;
$R^{12}$, independently from R6, is defined as $R^6$;
$R^{13}$ is selected from the group consisting of:
H; $C_1$–$C_6$-alkyl; unsubstituted and substituted phenyl, benzyl, heteroaryl, ($C_1$–$C_6$-alkyl)—CO—, phenyl-CO—, and heteroaryl-CO—, the substituents of which are selected from the group consisting of halogen, —CN, $C_1$–$C_3$-alkyl, $C_1$–$C_3$-alkoxy and $CF_3$, wherein one or more of these substituents can be present;

$R^{14}$, independently from $R^{13}$, is defined as $R^{13}$;
$R^{15}$ is selected from the group consisting of:
H; $C_1$–$C_{10}$-alkyl; ($C_1$–$C_3$-alkoxy)—$C_1$–$C_3$-alkyl- and substituted and unsubstituted benzyl, phenyl and heteroaryl, the substituents of which are selected from the group consisting of halogen, —CN, $C_1$–$C_3$-alkyl, $C_1$–$C_3$-alkoxy and $CF_3$, wherein one or more of these substituents can be present;

$R^{16}$ is selected from the group consisting of:
$C_1$–$C_{10}$-alkyl which can be substituted by one or more substituents selected from the group consisting of F, OH, $C_1$–$C_8$-alkoxy, aryloxy, $C_1$–$C_8$-alkylmercapto, $C_1$–$C_8$-alkylamino and di($C_1$–$C_8$-alkyl)amino; $CF_3$; and substituted and unsubstituted phenyl and heteroaryl, the substituents of which are selected from the group consisting of halogen, —CN, $C_1$–$C_3$-alkyl, $C_1$–$C_3$-alkoxy and $CF_3$, wherein one or more of these substituents can be present;

$R^{17}$, independently from $R^7$, is defined as $R^7$;
$R^{18}$, independently from $R^8$, is defined as $R^8$;
$R^{19}$, independently from $R^{16}$, is defined as $R^{16}$;
$R^{20}$, independently from $R^{16}$, is defined as $R^{16}$;
$R^{21}$, independently from $R^6$, is defined as $R^6$;
$R^{22}$, independently from $R^7$, is defined as $R^7$;
$R^{23}$, independently from $R^8$, is defined as $R^8$;
$R^{24}$, independently from $R^7$, is defined as $R^7$;
$R^{25}$, independently from $R^8$, is defined as $R^8$;
$R^{26}$, independently from $R^{16}$, is defined as $R^{16}$;
$R^{27}$, independently from $R^{16}$, is defined as $R^{16}$;

heteroaryl is a residue of a 5-membered to 10-membered, aromatic, monocyclic or bicyclic heterocycle containing one or more heteroatoms selected from the group consisting of N, O and S;

the group Hetar is a residue of a 5-membered to 10-membered, aromatic, monocyclic or bicyclic heterocycle containing one or more heteroatoms selected from the group consisting of N, O and S;

aryl is phenyl, naphth-1-yl or naphth-2-yl;

the group Ar is phenyl, naphth-1-yl or naphth-2-yl;

m is 0, 1 or 2;

n is 1, 2 or 3;

with the proviso that compounds of the formulae

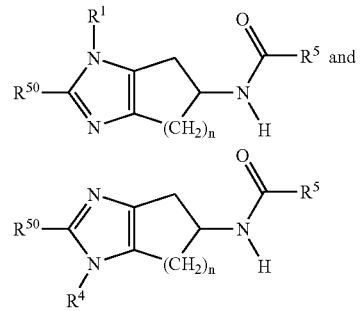

are excluded in which $R^{50}$ is selected from hydrogen, unsubstituted $C_1$–$C_6$-alkyl, $C_1$–$C_6$-alkoxy, unsubstituted $C_1$–$C_6$-alkylthio, halogen, —CN, $CF_3$, OH, amino, $C_1$–$C_6$-alkylamino and di($C_1$–$C_6$-alkyl)amino;

and compounds of the formulae

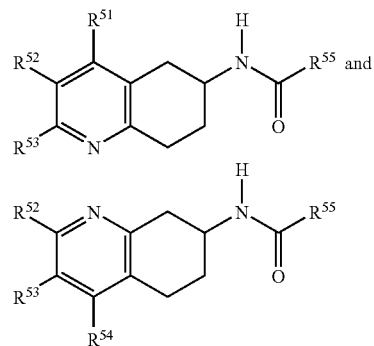

are excluded in which $R^{51}$, $R^{52}$, $R^{53}$ and $R^{54}$ are selected from hydrogen, unsubstituted or hydroxy-substituted $C_1$–$C_6$-alkyl, halogen, amino, $C_1$–$C_6$-alkylamino and di($C_1$–$C_6$-alkyl)amino, and $R^{55}$ is unsubstituted or substituted phenyl, thienyl, furyl, pyrrolyl or oxazolyl;

and the compound N-(2-amino-5,6,7,8-tetrahydro-4-hydroxyquinazolin-6-yl)-3,4-dichlorobenzamide is excluded.

If groups or substituents in the compounds of the formula I such as, for example, aryl, heteroaryl, alkyl etc., can be present several times, they all independently from each other have the meanings indicated and can hence, in each individual case, be identical with or different from each other. As an example the di($C_1$–$C_{10}$-alkyl)amino group may be mentioned in which the alkyl substituents can be identical or different. When a group in the compounds of the formula I can be at least monosubstituted, or when it carries one or more substituents, it can be substituted, for example, by one, two, three, four or five substituents. When a group is substituted by two or more substituents, the substituents can be identical or different from each other.

When a substituent group is defined in terms of another subsituent group, and these are indicated to be independent of each other, for example, as in the phrases, "$R^{10}$, independently from $R^7$, is $R^7$", or "$R^{10}$, independently from $R^7$, is defined as $R^7$", this means that they take on the same nature and range of values, but that they individually may be the same or different.

Alkyl, alkenyl and alkynyl residues can be linear or branched, acyclic or cyclic. This also applies when they are part of other groups, for example alkoxy groups, alkoxycarbonyl groups or substituted amino groups, or when they are substituted.

Examples of alkyl groups are methyl, ethyl, propyl, butyl, pentyl, hexyl, heptyl, octyl, nonyl, decyl, the n-isomers of these residues, isopropyl, isobutyl, isopentyl, sec-butyl, tert-butyl, neopentyl, 3,3-dimethylbutyl. The term alkyl here also expressly includes cycloalkyl groups and cycloalkyl-alkyl-groups, i. e., alkyl substituted by cycloalkyl, which groups contain at least three carbon atoms. Examples of such cycloalkyl residues are cyclopropyl, cyclobutyl, cyclopentyl, cyclohexyl, cycloheptyl and cyclooctyl. All cycloalkyl groups can be substituted by one or more identical or different $C_1$–$C_4$-alkyl residues, in particular by methyl. Examples of substituted cycloalkyl residues are 4-methylcyclohexyl, 4-tert-butylcyclohexyl or 2,3-dimethylcyclopentyl. Furthermore, unless stated otherwise, the term alkyl here also includes unsubstituted alkyl residues as well as alkyl residues which are substituted by one or more, for example 1, 2, 3 or 4, identical or different residues, for example aryl groups. In substituted alkyl residues, for example arylalkyl-, hydroxyalkyl- such as hydroxy-($C_1$–$C_3$)-alkyl- or alkoxyalkyl- such as $C_1$–$C_4$-alkyl-O—($C_1$–$C_3$)-alkyl-, the substituents can be present in any desired position.

Examples of alkenyl and alkynyl groups are vinyl, 1-propenyl, 2-propenyl, i.e. allyl, 2-butenyl, 2-methyl-2-propenyl, 3-methyl-2-butenyl, ethynyl, 2-propynyl, i.e. propargyl, 2-butynyl or 3-butynyl. The term alkenyl here also expressly includes cycloalkenyl groups and cycloalkenyl-alkyl-groups, i.e. alkyl substituted by cycloalkenyl, which groups contain at least three carbon atoms. Examples of cycloalkenyl residues are cyclopentenyl, cyclohexenyl, cycloheptenyl and cyclooctenyl. All cycloalkenyl groups can be substituted by one or more identical or different $C_1$–$C_4$-alkyl residues, in particular by methyl. Furthermore, unless stated otherwise, the terms alkenyl and alkynyl here also includes unsubstituted alkenyl and alkynyl residues as well as alkenyl and alkynyl residues which are substituted by one or more, for example 1, 2, 3 or 4, identical or different residues, for example aryl groups. In substituted alkenyl and alkynyl residues, for example arylalkenyl-, hydroxyalkenyl- such as hydroxy-($C_2$–$C_3$)-alkenyl- or alkoxyalkenyl- such as $C_1$–$C_3$-alkyl-O—($C_2$–$C_4$-alkenyl)-, the substituents can be present in any desired position.

Examples of $C_3$–$C_5$-alkandiyl are —$CH_2CH_2CH_2$—, —$CH_2$—$CH(CH_3)$—, —$CH_2CH_2CH_2CH_2$— and —$CH_2CH_2CH_2CH_2CH_2$— groups.

If not stated otherwise, the above-mentioned phenyl residues, naphthyl and indanyl residues and heterocyclic residues (including heteroaryl residues) can be unsubstituted or can carry one or more, for example 1, 2, 3 or 4, of the substituents indicated in the above definition which substituents can be present in any desired position. If in compounds of the formula I nitro groups are present as substituents, in a preferred embodiment of the invention in total only up to two nitro groups are present in the molecule. In monosubstituted phenyl residues the substituent can be in the 2-position, the 3-position or the 4-position, in disubstituted phenyl residues the substituents can be in 2,3-position, 2,4-position, 2,5-position, 2,6-position, 3,4-position or 3,5-position. In trisubstituted phenyl residues the substituents can be in 2,3,4-position, 2,3,5-position, 2,3,6-position, 2,4,5-position, 2,4,6-position or 3,4,5-position. In fourfold substituted phenyl residues, the substituents can be in the 2,3,4,5-position, the 2,3,4,6-position, or the 2,3,5,6-position. Tolyl (=methylphenyl) can be 2-tolyl, 3-tolyl or 4-tolyl. Naphthyl can be 1-naphthyl or 2-naphthyl. In monosubstituted 1-naphthyl residues the substituent can be in the 2-position, the 3-position, the 4-position, the 5-position, the 6-position, the 7-position or the 8-position, in monosubstituted 2-naphthyl residues in the 1-position, the 3-position, the 4-position, the 5-position, the 6-position, the 7-position or the 8-position. In higher substituted naphthyl residues, for example 1-naphthyl residues or 2-naphthyl residues which carry two or three substituents, the substituents can be present in any desired positions. Indanyl residues include indan-1-yl residues and indan-2-yl residues which can be unsubstituted or carry one or more of the substituents indicated. In case the indanyl residues are substituted, the substituent or substituents can be present in any of the positions possible.

Unless stated otherwise, heteroaryl residues and heterocyclic residues are preferably derived from heterocycles which contain 1, 2, 3 or 4 heteroatoms which can be identical or different; more preferably they are derived from heterocycles which contain 1, 2 or 3, in particular 1 or 2, heteroatoms which can be identical or different. Unless stated otherwise, the heterocycles can be monocyclic or polycyclic, for example monocyclic, bicyclic or tricyclic. Preferably they are monocyclic or bicyclic. The number of ring members preferably is 5, 6, 8, 9 or 10. The individual rings preferably are 5-membered rings, 6-membered rings or 7-membered rings. Examples of monocyclic and bicyclic heterocyclic systems from which residues occurring in the compounds of the formula I can be derived, are pyrrole, furan, thiophene, imidazole, pyrazole, 1,2,3-triazole, 1,2,4-triazole, 1,3-dioxole, 1,3-oxazole (=oxazole), 1,2-oxazole (=isoxazole), 1,3-thiazole (=thiazole), 1,2-thiazole (=isothiazole), tetrazole, pyridine, pyridazine, pyrimidine, pyrazine, pyran, thiopyran, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine, 1,3-thiazepine, indole, benzothiophene, benzofuran, benzothiazole, benzoxazole, benzimidazole, benzodioxole, quinoline, isoquinoline, cinnoline, quinazoline, quinoxaline, phthalazine, thienothiophenes, 1,8-naphthyridine and other naphthyridines, pteridin, or phenothiazine, each of them in saturated form (=perhydro form) or in partially unsaturated form, for example in the dihydro form or the tetrahydro form, or in maximally unsaturated form or aromatic form, provided that the respective forms are known and stable. The term "aryl" and the term "heteroaryl" as used herein comprise bicyclic residues in which both cycles are aromatic as well as bicyclic residues in which only one cycle is aromatic. The same applies to the term "group Ar" and the term "group Hetar". Suitable heterocycles include, for example, the saturated heterocycles pyrrolidine, piperidine, piperazine, morpholine and thiomorpholine. The degree of saturation of heterocyclic groups is indicated in their individual definitions. Unsaturated-heterocycles can contain, for example, 1, 2 or 3, double bonds within the ring system. 5-membered rings and 6-membered rings can in particular also be aromatic.

Residues derived from the mentioned heterocycles can be attached via any suitable carbon atom. Residues derived from nitrogen heterocycles which can carry a hydrogen atom or a substituent on a ring nitrogen atom, such as pyrrole, imidazole, pyrrolidine, morpholine or piperazine residues, can also be attached via a ring nitrogen atom, in particular if the respective heterocyclic residue is attached to a carbon atom. For example, a thienyl residue can be present as 2-thienyl residue or 3-thienyl residue, a furyl residue as 2-furyl residue or 3-furyl residue, a pyridinyl residue as 2-pyridinyl residue, 3-pyridinyl residue or 4-pyridinyl residue, a piperidinyl residue as 1-piperidinyl residue (=piperidino residue), 2-piperidinyl residue, 3-piperidinyl residue or 4-piperidinyl residue, a (thio)morpholinyl residue as 2-(thio)morpholinyl residue, 3-(thio)morpholinyl residue or 4-(thio)morpholinyl residue (=thiomorpholino residue). A residue derived from 1,3-thiazole or imidazole which is attached via a carbon atom can be attached via the 2-position, the 4-position or the 5-position.

In case a heterocyclic groups is substituted, it can carry one or more, for example 1, 2, 3 or 4, identical or different substituents. Substituents in heterocycles can be present in any desired positions, for example in a 2-thienyl residue or 2-furyl residue in the 3-position and/or in the 4-position and/or in the 5-position, in a 3-thienyl residue or 3-furyl residue in the 2-position and/or in the 4-position and/or in the 5-position, in a 2-pyridinyl residue in the 3-position and/or in the 4-position and/or in the 5-position and/or in the 6-position, in a 3-pyridinyl residue in the 2-position and/or in the 4-position and/or in the 5-position and/or in the 6-position, in a 4-pyridinyl residue in the 2-position and/or in the 3-position and/or in the 5-position and/or in the 6-position. Suitable nitrogen heterocycles can also be present as N-oxides or as quarternary salts containing a counterion which is derived from a pharmaceutically acceptable acid. Pyridine moieties, for example, can thus be present as pyridine-N-oxides.

Halogen is fluorine, chlorine, bromine or iodine, preferably fluorine or chlorine.

The present invention includes all stereoisomeric forms of the compounds of the formula I. Centers of asymmetry that are present in the compounds of formula I all independently from one another can have S configuration or R configuration. The invention includes all possible enantiomers and diastereomers and mixtures of two or more stereoisomers, for example mixtures of enantiomers and/or diastereomers, in all ratios. Thus, compounds of the present invention which can exist as enantiomers can be present in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. All these forms are a subject of the present invention. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the formula I or at the stage of an intermediate during the synthesis or at the stage of a starting compound. The present invention also includes all tautomeric forms of the compounds of formula I.

In case the compounds of formula I contain one or more acidic or basic groups, the invention also comprises their corresponding pharmaceutically or toxicologically acceptable salts, in particular their pharmaceutically utilizable salts. Thus, the compounds of the formula I which contain acidic groups can be present on these groups and can be used according to the invention, for example, as alkali metal salts, alkaline earth metal salts or as ammonium salts. Examples of such salts include sodium salts, potassium salts, calcium salts, magnesium salts or salts with ammonia or organic amines such as, for example, ethylamine, ethanolamine, triethanolamine or amino acids. Compounds of the formula I which contain one or more basic groups, i.e. groups which can be protonated, can be present and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid, and other acids known to the person skilled in the art. If the compounds of the formula I simultaneously contain acidic and basic groups in the molecule, the invention also includes, in addition to the salt forms mentioned, inner salts or betaines (zwitterions). The salts of the compounds of the formula I can be obtained by customary methods which are known to the person skilled in the art like, for example, by contacting the compound of the formula I with an organic or inorganic acid or base in a solvent or diluent, or by anion exchange or cation exchange from another salt. The present invention also includes all salts of the compounds of the formula I which, owing to low physiological compatibility, are not directly suitable for use in pharmaceuticals but which can be used, for example, as intermediates for chemical reactions or for the preparation of pharmaceutically acceptable salts.

The present invention furthermore includes all solvates of compounds of the formula I, for example hydrates and adducts with alcohols, active metabolites of the compounds of the formula I, and also derivatives and prodrugs of the compounds of the formula I which contain physiologically tolerable and cleavable groups, for example esters, amides and compounds in which the N—H group depicted in formula I is replaced with an N-alkyl group, such as N-methyl, or with an N-acyl group, such as N-acetyl or N-argininyl, including pharmaceutically acceptable salts formed on functional groups present in the N-acyl group.

In preferred embodiments of the present invention, one or more of the structural moieties in the compounds of formula I, including the number n, the ring A, the substituents $R^1$ to $R^5$ and the other groups present in the compounds of formula I, independently from each other have the following preferred meanings, more preferred meanings, even more preferred meanings or most preferred meanings.

In a preferred embodiment of the present invention the 5-membered or 6-membered monocyclic ring A which has two carbon atoms in common with the cycloalkenyl ring in formula I, is preferably selected from the following rings:

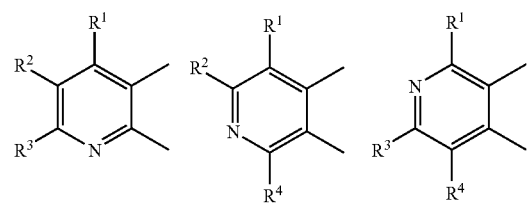

-continued

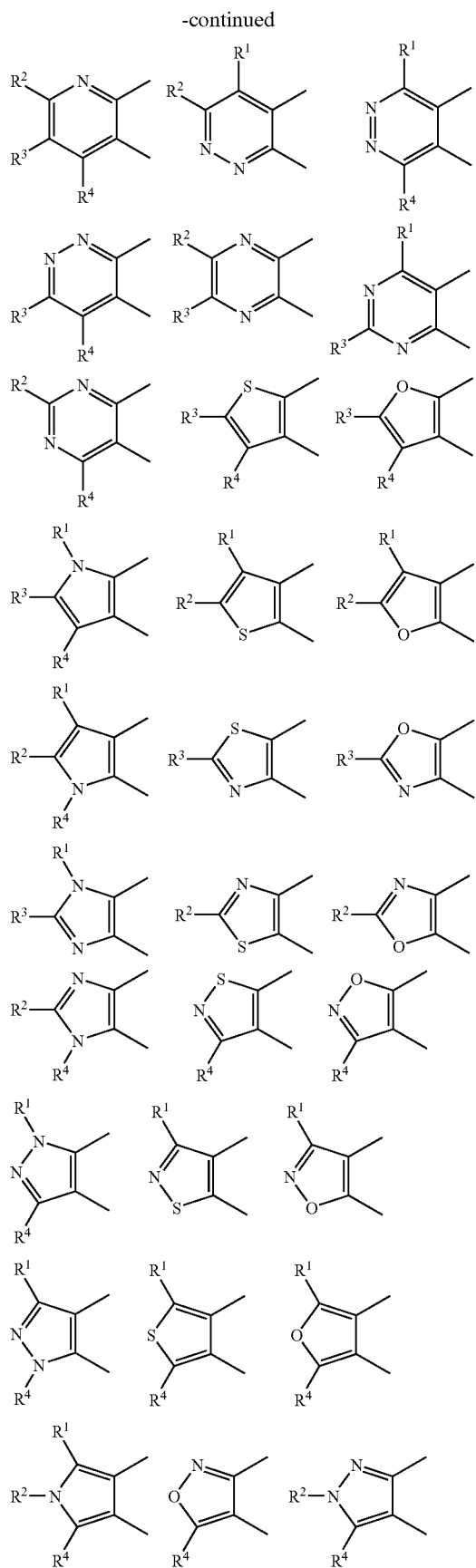

-continued

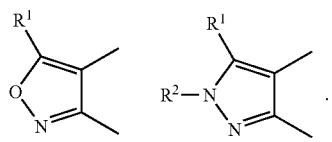

In the formulae of the specific rings A above and below the upper of the two free bonds is directed towards the $CH_2$ group in the condensed cycloalkenyl ring in formula I and the lower of the two free bonds is directed to the $(CH_2)_n$ group in formula I.

In another preferred embodiment of the present invention the ring A is an aromatic 6-membered ring containing 1 or 2 nitrogen atoms, in particular 1 nitrogen atom, as ring heteroatoms. In a further preferred embodiment of the present invention the ring A is an aromatic 5-membered ring containing a sulfur atom as ring heteroatom or a sulfur atom and a nitrogen atom as ring heteroatoms, in particular a ring containing a sulfur atom as ring heteroatom.

More preferably A is selected from the following rings:

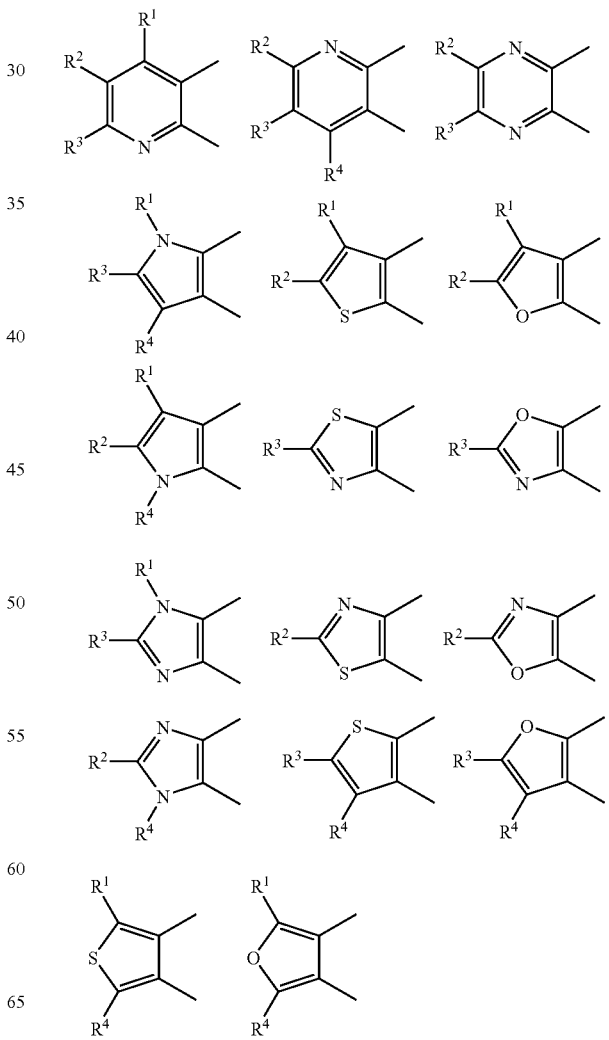

-continued

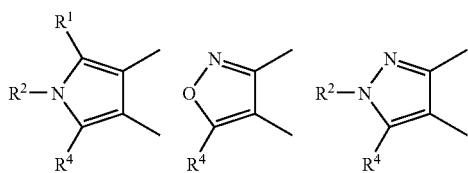

Even more preferably the ring A is selected from the following rings:

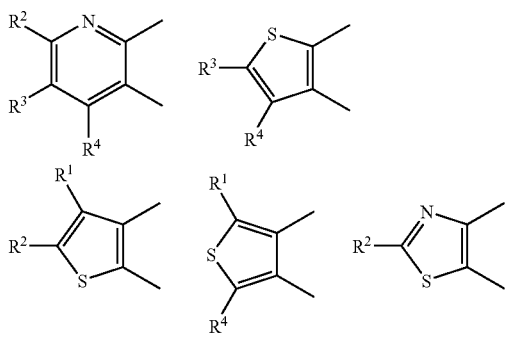

Most preferably the ring A is selected from the following rings:

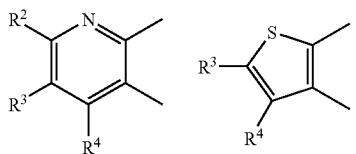

Thus, if one of the two most preferred rings A is present in the compounds of the formula I, the compounds of the formula I are the compounds of the formulae Ia or Ib, more specifically the 6,7-dihydro-5H-cyclopenta[b]pyridines of the formula Ic (also called pyrindines), the 5,6,7,8-tetrahydroquinolines of the formula Id (which may also be designated as 5,6,7,8-tetrahydrobenzo[b]pyridines), the 6,7,8,9-tetrahydro-5H-cyclohepta[b]pyridines of the formula Ie, the 5,6-dihydro-4H-cyclopenta[b]thiophenes of the formula If, the 4,5,6,7-tetrahydrobenzo[b]thiophenes of the formula Ig, or the 5,6,7,8-tetrahydro-4H-cyclohepta[b]thiophenes of the formula Ih, respectively. In the compounds of the formulae Ia to Ih the number n and the residues $R^2$ to $R^5$ can have any of the general or preferred or specific meanings indicated above or below.

Ia
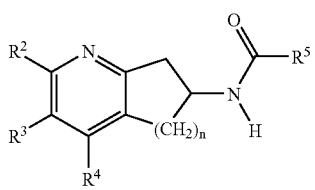

-continued

Ib
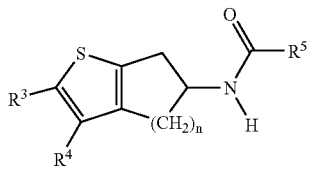

Ic
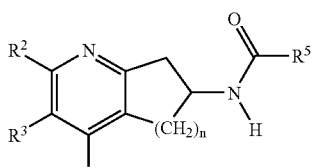

Id
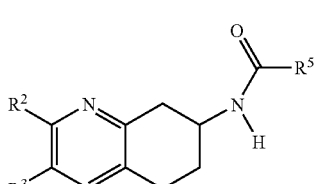

Ie
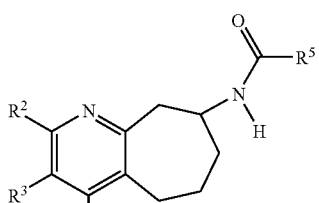

If
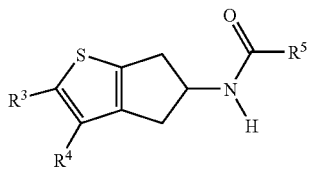

Ig
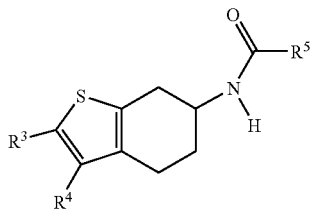

Ih
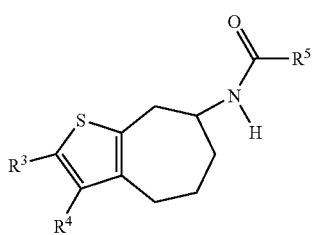

$R^1$ is preferably selected from the group consisting of: H; $C_1$–$C_4$-alkyl; $C_1$–$C_4$-alkoxy; $CF_3$; halogen; —CN; $C_1$–$C_4$-alkyl-$S(O)_m$—; and unsubstituted and at least monosubstituted phenyl and heteroaryl the substituents of which are selected from the group consisting of halogen, —CN, $C_1$–$C_3$-alkyl, $C_1$–$C_3$-alkoxy and $CF_3$, where heteroaryl is selected from the group consisting of 5-membered and 6-membered heterocycles containing one or more heteroatoms selected from the group consisting of N, O, and S. More preferably $R^1$ is H, halogen or $C_1$–$C_4$-alkyl.

$R^2$ is preferably selected from the group consisting of H, halogen, —CN and $C_1$–$C_4$-alkyl, more preferably from the group consisting of H, halogen and $C_1$–$C_4$-alkyl. Even more preferably $R^2$ is H.

$R^3$ is preferably selected from the group consisting of H, halogen, —CN, and $C_1$–$C_4$-alkyl, more preferably from the group consisting of H, halogen, and $C_1$–$C_4$-alkyl. Even more preferably $R^3$ is H.

$R^4$ is preferably selected from the group consisting of: H; $C_1$–$C_4$-alkyl; $C_1$–$C_4$-alkoxy; $CF_3$; halogen; —CN; $C_1$–$C_4$-alkyl-$S(O)_m$—; and unsubstituted and at least monosubstituted phenyl and heteroaryl the substituents of which are selected from the group consisting of halogen, —CN, $C_1$–$C_3$-alkyl, $C_1$–$C_3$-alkoxy and $CF_3$, where heteroaryl is selected from the group consisting of 5-membered and 6-membered heterocycles containing one or more heteroatoms selected from the group consisting of N, O, and S. More preferably $R^4$ is H, halogen or $C_1$–$C_4$-alkyl.

In particular each of $R^1$, $R^2$, $R^3$ and $R^4$ is H. As example of compounds in which $R^1$, $R^2$, $R^3$ and $R^4$ are H, the following compounds of the formulae Ii, Ik, Im, In, Io and Ip may be mentioned in which $R^5$ can have any of the general or preferred or specific meanings indicated above or below.

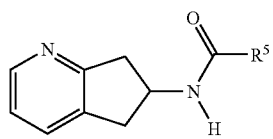

Ii

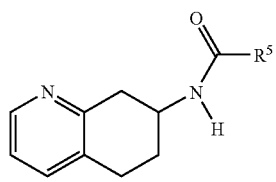

Ik

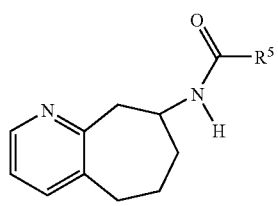

Im

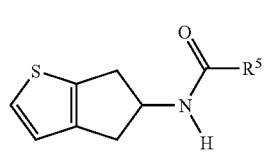

In

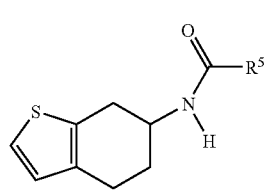

Io

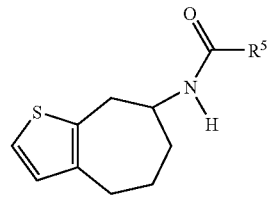

Ip $R^5$ is preferably a group Ar or a group Hetar both of which are unsubstituted or carry one or more identical or different substituents selected from the group consisting of: halogen; —CN; $NH_2$; unsubstituted and at least monosubstituted $C_1$–$C_8$-alkyl, $C_2$–$C_8$-alkenyl, $C_2$–$C_8$-alkynyl, $C_1$–$C_8$-alkoxy, $C_1$–$C_8$-alkylamino and di($C_1$–$C_8$-alkyl)amino, the substituents of which are selected from the group consisting of F, OH, $C_1$–$C_6$-alkoxy, phenoxy, $C_1$–$C_6$-alkylmercapto, $NH_2$, $C_1$–$C_6$-alkylamino and di($C_1$–$C_6$-alkyl)amino; $C_3$–$C_5$-alkandiyl; phenyl; heteroaryl; phenyl-substituted or heteroaryl-substituted $C_1$–$C_2$-alkyl; $CF_3$; OH; phenoxy; benzyloxy; ($C_1$–$C_6$-alkyl)—COO; $S(O)_m$—($C_1$–$C_6$)-alkyl which can optionally be substituted by OH or $C_1$–$C_6$-alkoxy; $S(O)_m$-phenyl; $S(O)_m$-heteroaryl; SH; phenylamino; benzylamino; ($C_1$–$C_6$-alkyl)—CONH—; ($C_1$–$C_6$-alkyl)—CON($C_1$–$C_4$-alkyl)—; phenyl-CONH—; phenyl-CON($C_1$–$C_4$-alkyl)—; heteroaryl-CONH—; heteroaryl-CON($C_1$–$C_4$-alkyl)—; ($C_1$–$C_6$-alkyl)—CO—; phenyl-CO—; heteroaryl-CO—; $CF_3$—CO—; —$OCH_2O$—; —$OCF_2O$—; —$OCH_2CH_2O$—; —$CH_2CH_2O$—; $COO(C_1$–$C_6$-alkyl); —$CONH_2$; —$CONH(C_1$–$C_6$-alkyl); —$CON(di(C_1$–$C_6$-alkyl))$; $C(NH)$—$NH_2$; —$SO_2NH_2$; —$SO_2NH(C_1$–$C_6$-alkyl); —$SO_2NH(phenyl)$; —$SO_2N(di(C_1$–$C_6$-alkyl))$; $C_1$–$C_6$-alkyl-$SO_2NH$—; ($C_1$–$C_6$-alkyl)—$SO_2N(C_1$–$C_6$-alkyl)—; phenyl-$SO_2NH$—; phenyl-$SO_2N(C_1$–$C_6$-alkyl)—; heteroaryl-$SO_2NH$—; heteroaryl-$SO_2N(C_1$–$C_6$-alkyl)—; and a residue of a saturated or at least monounsaturated aliphatic, mononuclear 5-membered to 7-membered heterocycle containing 1, 2 or 3 heteroatoms selected from the group consisting of N, O and S, which heterocycle can be substituted by one or more substituents selected from the group consisting of halogen, $C_1$–$C_3$-alkyl, $C_1$–$C_3$-alkoxy, OH, oxo and $CF_3$, where said heterocycle can optionally be condensed to the said group Ar or the said group Hetar; wherein all heteroaryl, phenyl, heteroaryl-containing and phenyl-containing groups, which are optionally present in the said substituents of the said group Ar or the said group Hetar, can be substituted by one or more substituents selected from the group consisting of halogen, —CN, $C_1$–$C_3$-alkyl, OH, $C_1$–$C_3$-alkoxy, and $CF_3$.

$R^5$ is more preferably phenyl or a group Hetar both of which are unsubstituted or carry one or more identical or different substituents selected from the group consisting of: halogen; —CN; $NH_2$; unsubstituted and at least monosubstituted $C_1$–$C_6$-alkyl, $C_2$–$C_6$-alkenyl, $C_2$–$C_6$-alkynyl, $C_1$–$C_3$-alkoxy, $C_1$–$C_4$-alkylamino and di($C_1$–$C_4$-alkyl)amino, the substituents of which are selected from the group consisting of F, $C_1$–$C_3$-alkoxy, $C_1$–$C_3$-alkylmercapto and $NH_2$; $C_3$–$C_5$-alkandiyl; phenyl; heteroaryl; phenyl-substituted or heteroaryl-substituted $C_1$–$C_2$-alkyl; $CF_3$; OH; ($C_1$–$C_4$-alkyl)—COO; $S(O)_m$—($C_1$–$C_4$)-alkyl; ($C_1$–$C_4$-alkyl)—CONH—; ($C_1$–$C_4$-alkyl)—CON($C_1$–$C_4$-alkyl)—; ($C_1$–$C_4$-alkyl)—CO—; phenyl-CO—; heteroaryl-CO—; $CF_3$-CO—; —$OCH_2O$—; —$OCF_2O$—; —$OCH_2CH_2O$—; —$CH_2CH_2O$—; $COO(C_1$–$C_6$-alkyl); —$CONH_2$; —CONH (C$_1$–C$_4$-alkyl); —CON(di(C$_1$–C$_4$-alkyl)); C(NH)—NH$_2$; —SO$_2$NH$_2$; —SO$_2$NH(C$_1$–C$_4$-alkyl); —SO$_2$NH(phenyl); —SO$_2$N(di(C$_1$–C$_4$-alkyl)); (C$_1$–C$_4$-alkyl)—SO$_2$NH—; (C$_1$–C$_4$-alkyl)—SO$_2$N(C$_1$–C$_4$-alkyl)—; and a residue of a saturated or at least monounsaturated aliphatic, mononuclear 5-membered to 7-membered heterocycle containing 1, 2 or 3 heteroatoms selected from the group consisting of N, O and S, which heterocycle can be substituted by one or more substituents selected from the group consisting of halogen, C$_1$–C$_3$-alkyl, C$_1$–C$_3$-alkoxy, OH, oxo and CF$_3$, where said heterocycle can optionally be condensed to the said phenyl or the said group Hetar; wherein all heteroaryl, phenyl, heteroaryl-containing and phenyl-containing groups, which are optionally present in the said substituents of the said phenyl or the said group Hetar, can be substituted by one or more substituents selected from the group consisting of halogen, —CN, C$_1$–C$_3$-alkyl, OH, C$_1$–C$_3$-alkoxy, and CF$_3$.

R$^5$ is even more preferably phenyl or a group Hetar both of which are unsubstituted or carry one or more identical or different substituents selected from the group consisting of: F; Cl; Br; C$_1$–C$_3$-alkyl; C$_1$–C$_3$-alkoxymethyl; 2-amino-3,3,3-trifluoropropyl-; CF$_3$; C$_3$–C$_5$-alkandiyl; phenyl; heteroaryl; benzyl; heteroaryl-methyl-; OH; C$_1$–C$_3$-alkoxy; phenoxy; trifluoromethoxy; 2,2,2-trifluoroethoxy; (C$_1$–C$_4$-alkyl)—COO—; C$_1$–C$_3$-alkylmercapto; phenylmercapto; C$_1$–C$_3$-alkylsulfonyl; phenylsulfonyl; NH$_2$; C$_1$–C$_4$-alkylamino; di(C$_1$–C$_4$-alkyl)amino; (C$_1$–C$_3$-alkyl)—CONH—; (C$_1$–C$_3$-alkyl)—SO$_2$NH—; (C$_1$–C$_3$-alkyl)—CO—; phenyl-CO—; —OCH$_2$O—; —OCF$_2$O—; —CH$_2$CH$_2$O—; COO (C$_1$–C$_4$-alkyl); —CONH$_2$; —CONH(C$_1$–C$_4$-alkyl); —CON (di(C$_1$–C$_4$-alkyl)); —CN; —SO$_2$NH$_2$; —SO$_2$NH(C$_1$–C$_4$-alkyl); —SO$_2$N(di(C$_1$–C$_4$-alkyl)); pyrrolidinyl; piperidinyl; morpholinyl and thiomorpholinyl; wherein all heteroaryl, phenyl, heteroaryl-containing and phenyl-containing groups, which are optionally present in the said substituents of the said phenyl or the said group Hetar, can be substituted by one or more substituents selected from the group consisting of halogen, —CN, C$_1$–C$_3$-alkyl, OH, C$_1$–C$_3$-alkoxy, and CF$_3$.

R$^5$ is most preferably selected from the group consisting of 4-fluorophenyl, 4-chlorophenyl, 4-bromophenyl, 4-(C$_1$–C$_3$-alkoxy)-phenyl, 4-trifluoromethoxyphenyl, 2-bromo-4-fluorophenyl, 2-chloro-4-fluorophenyl, 3,4-dimethylphenyl, 2,4-dimethylphenyl, 4-chloro-2-methylphenyl, 2-hydroxy-4-methylphenyl, 2-hydroxy-4-ethoxyphenyl, 2-methoxy4-methylphenyl, 4-phenoxyphenyl, 3-fluoro-4-methylphenyl, benzo[1,3]dioxol-5-yl, 2,2-difluoro-benzo[1,3]dioxol-5-yl, 2,3-dihydrobenzofuran-5-yl, 1-(4-chlorophenyl)-5-trifluoromethyl-1H-pyrazol-4-yl, 1-(4-fluorophenyl)-3,5-dimethyl-1H-pyrazol-4-yl, 1H-benzotriazol-5-yl, 1H-indol-4-yl, 1H-indol-6-yl, 1-isopropyl-2-trifluoromethyl-1H-benzimidazol-5-yl, 1-methyl-3-oxo-1,2,3,4-tetrahydro-quinoxalin-6-yl, 1-phenyl-5-trifluoromethyl-1H-pyrazol-4-yl, 2-(2-hydroxypyridin-4-yl)-1H-benzimidazol-5-yl, 2-(4-cyanophenyl)-1H-benzimidazol-5-yl, 2,4-dimethyloxazol-5-yl, 2,4-dimethylpyrimidin-5-yl, 2,4-dimethylthiazol-5-yl, 2,5-dimethyl-1H-pyrrol-3-yl, 2,5-dimethyl-1-phenyl-1H-pyrrol-3-yl, 2,5-dimethyl-1-(pyridin-4-ylmethyl)-1H-pyrrol-3-yl, 2,5-dimethyl-2H-pyrazol-3-yl, 2,6-dichloropyridin-3-yl, 2,6-dimethoxypyridin-3-yl, 2,6-dimethylpyridin-3-yl, 2-amino-4,6-dimethylpyridin-3-yl, 2-amino-6-chloropyridin-3-yl, 2-aminopyridin-3-yl, 2-chloro-6-methylpyridin-3-yl, 2-chloropyridin-4-yl, 2-cyclopropyl-4-methylthiazol-5-yl, 2-dimethylamino-4-methylthiazol-5-yl, 2-dimethylaminopyridin-4-yl, 2-ethyl-5-methyl-2H-pyrazol-3-yl, 2-hydroxy-6-methylpyridin-3-yl, 2-methyl-1H-benzimidazol-5-yl, 2-methyl-3H-benzimidazol-5-yl, 2-methylpyridin-3-yl, 2-methyl-6-trifluoromethylpyridin-3-yl, 2-methylthiazol-5-yl, 2-(morpholin-4-yl)-pyridin-4-yl, 2-(morpholin-4-yl)-pyrimidin-5-yl, 2-(pyrrolidin-1-yl)-pyridin-4-yl, 3,5-dimethyl-1H-pyrazol-4-yl, 3-amino-5,6-dimethylpyrazin-2-yl, 3-amino-5-methylpyrazin-2-yl, 3-aminopyrazin-2-yl, 3-dimethylamino-4-methylphenyl, 3-dimethylaminophenyl, 3H-benzimidazol-5-yl, 1H-benzimidazol-5-yl, 3-methylsulfonylamino-2-methylphenyl, 3-methylsulfonylaminophenyl, 3-methylisoxazol-4-yl, 3-(morpholin-4-yl)-phenyl, 3-(piperidin-1-yl)-phenyl, 3-(pyrrolidin-1-yl)-phenyl, 4-(2,2,2-trifluoroethoxy)phenyl, 4,6-dimethylpyridin-3-yl, 4-amino-2-ethylsulfanylpyrimidin-5-yl, 4-amino-2-methylpyrimidin-5-yl, 4-chloro-3-methylsulfonylaminophenyl, 4-chloro-3-sulfamoylphenyl, 4-methyl-3-methylaminophenyl, 4-methylthiazol-5-yl, pyridin-2-yl, 5,6,7,8-tetrahydroquinolin-3-yl, 5-amino-1-phenyl-1H-pyrazol-4-yl, 5-methylsulfonyl-2-methylphenyl, 5-methyl-1-phenyl-1H-pyrazol-4-yl, 5-methylisoxazol-3-yl, 5-methylpyridin-3-yl, 5-methylpyrazin-2-yl, 6-chloropyridin-3-yl, 6-cyanopyridin-3-yl, 6-dimethylaminopyridin-3-yl, 6-ethynylpyridin-3-yl, 6-methoxymethylpyridin-3-yl, 6-methoxypyridin-3-yl, 6-methyl-2-methylaminopyridin-3-yl, 6-methylaminopyrazin-2-yl, 6-methylpyridin-3-yl, 6-(morpholin-4-yl)-pyridin-3-yl, 6-(pyrrolidin-1-yl)-pyridin-3-yl, imidazo[1,2-a]pyridin-2-yl, 6-trifluoromethylpyridin-3-yl, pyrimidin-4-yl, 4-methylsulfanylphenyl, 4-ethylsulfanylphenyl, 3-methoxycarbonylphenyl, 4-methoxycarbonylphenyl, 3-ethoxycarbonylphenyl, 4-ethoxycarbonylphenyl, 2-bromo-4-chlorophenyl, 2,3-dichlorophenyl, 3-chloro-4-(isopropylsulfonyl) thiophen-2-yl, 4-bromo-2-chlorophenyl, 4-methoxyphenyl, 4-ethoxyphenyl, 3-methoxyphenyl, 3-ethoxyphenyl, 2-methyl-thiophen-3-yl, 3-chloro-4-methyl-thiophen-2-yl, 5-bromo-thiophen-2-yl, 5-chloro-thiophen-2-yl, 5-methyl-thiophen-2-yl, 4-methyl-thiophen-2-yl, 3-methyl-thiophen-2-yl, 5-acetyl-thiophen-2-yl, pyridin-3-yl, pyridin-4-yl, 4-trifluoromethylphenyl, 4-ethylaminophenyl, 4-methylaminophenyl, 2-aminophenyl, 4-bromo-2-fluorophenyl, 2-chlorophenyl, 3-chloro-4-methylphenyl, 4-chloro-3-methylphenyl, 2-chloro-3-methylphenyl, 2-methyl phenyl, 2-acetoxy-4-methylphenyl, 2-acetoxy-4-ethoxyphenyl, 2-acetoxy-4-methoxyphenyl, 4-trifluoromethylsulfanylphenyl, naphthalen-2-yl, 1,1-dimethylindan-4-yl, 3-isobutyrylaminophenyl, 3-(2,2-dimethylpropionylamino)phenyl, 2-bromophenyl, 2-fluorophenyl, 3-bromo-5-methylthiophen-2-yl, 3-chloro-6-fluorobenzo[b]thiophen-2-yl and 3,4-dichlorobenzo[b]thiophen-2-yl.

Heteroaryl is preferably a residue of a 5-membered to 10-membered, aromatic, monocyclic or bicyclic heterocycle containing 1, 2 or 3 heteroatoms selected from the group consisting of N, O and S. More preferably heteroaryl is selected from the group consisting of furyl, pyrrolyl, thienyl, thiazolyl, isothiazolyl, oxazolyl, isoxazolyl, pyrazolyl, imidazolyl, pyridazinyl, pyrazinyl, pyridinyl, pyrimidinyl, benzimidazolyl, benzothiazolyl, benzoxazolyl, quinolinyl, isoquinolinyl, quinoxalinyl, quinazolinyl, indolyl, benzofuranyl, benzodioxolyl, benzothiophenyl and indazolyl.

The group Hetar is preferably a residue of a 5-membered to 10-membered, aromatic, mono- or bicyclic heterocycle containing 1, 2 or 3 heteroatoms selected from the group consisting of N, O and S. More preferably the group Hetar is selected from the group consisting of furyl, pyrrolyl, thienyl, thiazolyl, isothiazolyl, oxazolyl, isoxazolyl, pyrazolyl, imidazolyl, pyridazinyl, pyrazinyl, pyridinyl, pyrimidinyl, benzimidazolyl, benzothiazolyl, benzoxazolyl, quinolinyl, isoquinolinyl, quinoxalinyl, quinazolinyl, indolyl, benzofuranyl, benzodioxolyl, benzothiophenyl and indazolyl.

Aryl is preferably phenyl.

m is preferably 0 or 2.

n is preferably 1 or 3. I.e., in a preferred embodiment of the invention the compounds of formula I are acylated heteroaryl-condensed cyclopentenylamines of the formula Iq (also designated as cyclopenta-condensed heteroarene derivatives), or acylated heteroaryl-condensed cycloheptenylamines of the formula Ir (also designated as cyclohepta-condensed heteroarenes). In the compounds of the formulae Iq and Ir the ring A and the residues $R^1$ to $R^5$ can have any of the general or preferred or specific meanings indicated above or below.

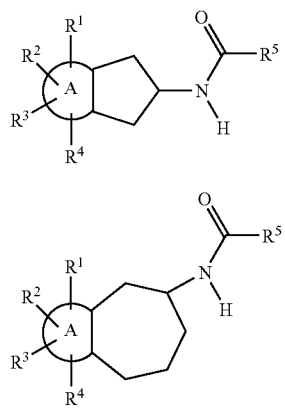

Preferred compounds of the formula I are those compounds in which one or some or all of the structural moieties and groups contained therein have preferred meanings, more preferred meanings, even more preferred meanings or most preferred meanings defined above, all combinations of such preferred meanings etc. and/or of specific meanings of a group being a subject of the present invention. With respect to all preferred compounds of the formula I the present invention also includes all stereoisomeric forms and mixtures thereof in all ratios, and their pharmaceutically acceptable salts.

As examples of specific compounds, which are a subject of the present invention in all their stereoisomeric forms and in the form of mixtures thereof in all ratios, and in the form of their pharmaceutically acceptable salts, the following compounds may be mentioned:

4-fluoro-N-(6,7,8,9-tetrahydro-5H-cyclohepta[b]pyridin-8-yl)benzamide,
4-chloro-N-(6,7,8,9-tetrahydro-5H-cyclohepta[b]pyridin-8-yl)benzamide,
2,4-dimethyl-N-(6,7,8,9-tetrahydro-5H-cyclohepta[b]pyridin-8-yl)benzamide,
2,4-dichloro-N-(6,7,8,9-tetrahydro-5H-cyclohepta[b]pyridin-8-yl)benzamide,
2,2-difluorobenzo[1,3]dioxole-5-carboxylic acid (6,7,8,9-tetrahydro-5H-cyclohepta[b]pyridin-8-yl)amide,
2,6-dimethyl-N-(6,7,8 ,9-tetrahydro-5H-cyclohepta[b]pyridin-8-yl)nicotinamide,
6-methoxymethyl-N-(6,7,8,9-tetrahydro-5H-cyclohepta[b]pyridin-8-yl)nicotinamide,
6-methoxy-N-(6,7,8,9-tetrahydro-5H-cyclohepta[b]pyridin-8-yl)nicotinamide,
2,5-dimethyl-1-phenyl-1H-pyrrole-3-carboxylic acid (6,7,8,9-tetrahydro-5H-cyclohepta[b]pyridin-8-yl)amide,
2-methyl-1H-benzimidazole-5-carboxylic acid (6,7,8,9-tetrahydro-5H-cyclohepta[b]pyridin-8-yl)amide,
2,5-dimethyl-1-(pyridin-4-ylmethyl)-1H-pyrrole-3-carboxylic acid (6,7,8,9-tetrahydro-5H-cyclohepta[b]pyridin-8-yl)amide,
2,4-dichloro-N-(6,7-dihydro-5H-[1]pyrindin-6-yl)benzamide,
2,5-dimethyl-1-phenyl-1H-pyrrole-3-carboxylic acid (6,7-dihydro-5H-[1]pyrindin-6-yl)amide,
2,5-dimethyl-1-(pyridin-4-ylmethyl)-1H-pyrrole-3-carboxylic acid (6,7-dihydro-5H-[1]pyrindin-6-yl)amide,
N-(5,6-dihydro-4H-cyclopenta[b]thiophen-5-yl)-4-fluorobenzamide,
4-chloro-N-(5,6-dihydro-4H-cyclopenta[b]thiophen-5-yl)benzamide,
N-(5,6-dihydro-4H-cyclopenta[b]thiophen-5-yl)-2,4-dimethylbenzamide,
2,4-dichloro-N-(5,6-dihydro-4H-cyclopenta[b]thiophen-5-yl)benzamide,
2,2-difluorobenzo[1,3]dioxole-5-carboxylic acid (5,6-dihydro-4H-cyclopenta[b]thiophen-5-yl)amide,
N-(5,6-dihydro-4H-cyclopenta[b]thiophen-5-yl)-2,6-dimethylnicotinamide,
N-(5,6-dihydro-4H-cyclopenta[b]thiophen-5-yl)-6-methoxymethylnicotinamide,
N-(5,6-dihydro-4H-cyclopenta[b]thiophen-5-yl)-6-methoxynicotinamide,
2,5-dimethyl-1-phenyl-1H-pyrrole-3-carboxylic acid (5,6-dihydro-4H-cyclopenta[b]thiophen-5-yl)amide,
2-methyl-1 H-benzimidazole-5-carboxylic acid (5,6-dihydro-4H-cyclopenta[b]thiophen-5-yl)amide,
2,5-dimethyl-1-(pyridin-4-ylmethyl)-1H-pyrrole-3-carboxylic acid (5,6-dihydro-4H-cyclopenta[b]thiophen-5-yl)amide.

A compound of the formula I or a salt thereof can be prepared, for example, by a process which comprises the acylation of a heteroaryl-condensed cycloalkenylamine of the formula II with a carboxylic acid of the formula $R^5$—COOH or a derivative thereof, which process also is a subject of the present invention.

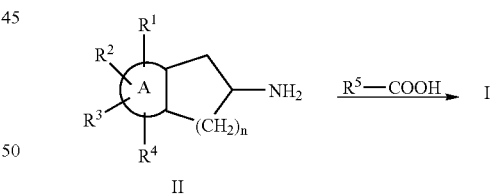

Suitable derivatives of the carboxylic acids of the formula $R^5$—COOH are, for example, carboxylic acid chlorides, esters including $C_1$–$C_4$-alkyl esters, such as methyl esters or ethyl esters, optionally substituted aryl esters, such as phenyl esters or nitrophenyl esters, or activated esters, or anhydrides or mixed anhydrides. In the compounds of the formula II and the carboxylic acids of the formula $R^5$—COOH and their derivatives the ring A, the number n and the groups $R^1$, $R^2$, $R^3$, $R^4$ and $R^5$ have the meanings indicated above with respect to the compounds of the formula I, or else functional groups can be present in protected form or in the form of a precursor. For example, when a compound of the formula I is to be prepared which contains a carboxylic acid group or an amino group, it may be appropriate that in the acylation reaction these groups are present in protected form, for example as an ester such as a tert-butyl ester or benzyl ester instead of the free carboxylic acid group, or as an acylated amino group such as a tert-butoxycarbonylamino group or benzyloxycarbonylamino group instead of the free amino group, and only subsequent to the acylation the desired final groups are liberated by deprotection. Suitable protective group strategies which may be used in the synthesis of the compounds of formula I are known to the person skilled in the art. An example of a precursor group of a functional group is the nitro group which can be converted into an amino group by reduction, for example by catalytic hydrogenation, after the acylation reaction.

The acylation reactions can be carried out under standard conditions known to the person skilled in the art. In many cases the reaction is favorably performed in an inert solvent or diluent, for example a hydrocarbon or a chlorinated hydrocarbon, such as toluene, 1,2-dichloroethane or methylene chloride, an ether, such as tetrahydrofuran, dioxane or 1,2-dimethoxyethane, an alcohol such as methanol, ethanol or isopropanol, an amide such as N,N-dimethylformamide or N-methylpyrrolidone, acetonitrile, water, or a else a mixture of two or more solvents or diluents. Depending on the individual case, it may be advantageous to perform the reaction in the presence of a base, for example an inorganic base such as sodium hydroxide, sodium carbonate or sodium hydrogencarbonate, or an organic base such as triethylamine, ethyldiisopropylamine, N-ethylmorpholine or pyridine, and/or in the presence of an acylation catalyst such as 4-dimethylaminopyridine.

If a carboxylic acid of the formula $R^5$—COOH is to be used in the acylation of a compound of the formula II, it is often advantageous to activate the acid or a salt thereof with a condensation agent or coupling agent, for example an agent like those commonly used in peptide chemistry for the formation of amide bonds. Examples of suitable coupling agents are carbodiimides such as dicyclohexylcarbodiimide or diisopropylcarbodiimide, TOTU, i.e. O-((cyano(ethoxycarbonyl)methylene)amino)-N,N,N',N'-tetramethyluronium tetrafluoroborate, HATU, i. e. O-(7-azabenzotriazol-1-yl)-1,1,3,3-tetramethyluronium hexafluorophosphate, chloroformic acid esters like ethyl chloroformate or isobutyl chloroformate, tosyl chloride, propylphosphonic acid anhydride or carbonyldiimidazole. Depending on the individual case, the suitable reaction temperature may lie within a wide range. For example, when employing into the acylation reaction a carboxylic acid in the presence of a coupling agent or a carboxylic acid chloride, the reaction can often be carried out at room temperature.

Subsequent to the acylation reaction, besides the above-mentioned deprotection of protected groups or the conversion of a precursor group into the desired final group, optionally further functionalizations or modifications of the obtained compounds can be carried out and suitable functional groups can, for example, be esterified, amidated, transesterified, hydrolyzed, alkylated, sulfonylated, acylated, reduced, oxidized, converted into a salt, or subjected to other reactions.

The starting compounds for the preparation of the compounds of the formula I are commercially available or can be prepared according to or analogously to literature procedures. Routes for the preparation of the compounds of formula II include, for example, the conversion of a ketone of the formula III into an oxime of the formula IV and the conversion of the latter into a compound of the formula II, and the conversion of a carboxylic acid of the formula V into a carboxylic acid azide of the formula VI and the conversion of the latter into a compound of the formula II. The mentioned conversions can be carried out under standard conditions known to the person skilled in the art. For example, a ketone of the formula III can be converted into an oxime of the formula IV by treatment with an organic nitrite such as isoamyl nitrite in the presence of hydrochloric acid, and the reduction of the oxime group to give the amino group and the reduction of the C=O group in benzylic position to give the $CH_2$ group can be accomplished simultaneously by catalytic hydrogenation in the presence of, for example, palladium. A carboxylic acid of the formula V can be converted into a carboxylic acid azide of the formula VI by reaction with diphenylphosphoryl azide, for example, and the latter be subjected to a Curtius rearrangement.

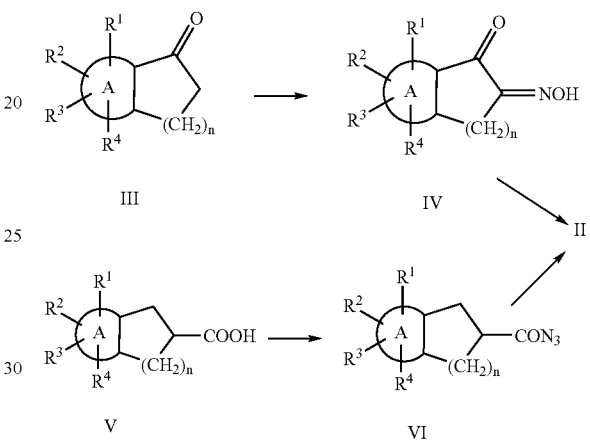

The starting compounds of the formulae III and V can be obtained as described, for example, in JP 2-255664, EP 853083; U.S. Pat. No. 6,258,829; U.S. Pat. No. 6,278,027; CA 2151443; GB 2280438; Schenone et al., J. Heterocycl. Chem. 19 (1982) 1355; Bianchi et al., J. Chem. Res., Synop., (1981) 6; Muraro et al., Bull. Soc. Chim. Fr., Pt. 2, (1973) 335; Muraro et al., C. R. Acad. Sci., Ser. C, 273 (1971) 1362; MacDowell et al., J. Org. Chem. 32 (1967) 1226; Ravina et al., J. Med. Chem. 42 (1999) 2774; Nayyar et al., J. Org. Chem. 62 (1997) 982; Binder et al., Monatsh. Chem. 129 (1998) 887; Westerwelle et al., Chem. Ber. 124 (1991) 571; Huang et al., Synth. Commun. 28 (1998) 1197; Reimann et al., Pharmazie 50 (1995) 589; Caprathe et al., J. Med. Chem. 34 (1991) 2736; Hoffman et al., J. Org. Chem. 49 (1984) 193; Schroeder et al., Eur. J. Med. Chem.—Chim. Ther. 14 (1979) 309; Ruangsiyanand et al., Chem. Ber. 103 (1970) 2403; Dammertz et al., Arch. Pharm. 310 (1977) 172; Hicks et al., J. Chem. Soc., Perkin Trans. 1, (1984) 2297; Jones et al., J. Chem. Soc., Perkin Trans. 1, (1973) 968; U.S. Pat. No. 5,753,662 or WO 94/04531 (the content of each of which is incorporated herein by reference), or by using methods analogous to those described in these references.

All reactions for the synthesis of the compounds of the formula I are per se wellknown to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York, the content of each of which is incorporated by reference. As mentioned above, depending on the circumstances of the individual case, in order to avoid side reactions during the synthesis of a compound of the formula I, in any reaction step it can be necessary or advantageous to temporarily block functional groups by introducing protective groups and to deprotect them in a later stage of the synthesis, or introduce functional groups in the form of precursor groups which in a later reaction step are converted into the desired functional groups. Such synthesis strategies and protective groups and precursor groups which are suitable in an individual case are known to the skilled person. If desired, the compounds of the formula I can be purified by customary purification procedures, for example by recrystallization or chromatography.

The compounds of the formula I are useful pharmaceutically active compounds which upregulate the expression of endothelial NO synthase and can be employed as medicaments for the treatment of various diseases. In the context of the present invention, treatment is understood as comprising both therapy, including alleviation and cure, of disease symptoms and prevention or prophylaxis of disease symptoms, such as, for example, the prevention of the appearance of asthmatic disease symptoms or the prevention of myocardial infarction or of myocardial reinfarction in relevant patients. The diseases or disease symptoms can be acute or chronic. Diseases which can be treated with the compounds of the formula I include, for example, cardiovascular diseases like stable and unstable angina pectoris, coronary heart disease, Prinzmetal angina (spasm), acute coronary syndrome, heart failure, myocardial infarction, stroke, thrombosis, peripheral artery occlusive disease (PAOD), endothelial dysfunction, atherosclerosis, restenosis, endothel damage after PTCA, hypertension including essential hypertension, pulmonary hypertension and secondary hypertension (renovascular hypertension, chronic glomerulonephritis), erectile dysfunction and ventricular arrhythmia. Further, the compounds of the formula I lower the cardiovascular risk of postmenopausal women and of women taking contraceptives. Compounds of the formula I can additionally be used in the treatment, i. e. the therapy and prevention, of diabetes and diabetes complications (nephropathy, retinopathy), angiogenesis, asthma bronchiale, chronic renal failure, cirrhosis of the liver, osteoporosis, restricted memory performance or a restricted ability to learn. Preferred indications are stable angina pectoris, coronary heart disease, hypertension, endothelial dysfunction, atherosclerosis and diabetes complications.

As used above, and throughout the description of the invention, the following terms, unless otherwise indicated, shall be understood to have the following meanings.

"Patient" includes both human and other mammals.

"Pharmaceutically effective amount" is meant to describe an amount of compound, composition, medicament or other active ingredient effective in producing the desired therapeutic effect.

The compounds of the formula I can be used in combination with other pharmaceutically active compounds, preferably with compounds which are able to enhance the effect of the compounds of the formula I. Examples of such other compounds include statins; ACE inhibitors; AT1 antagonists; argininase inhibitors; PDE V inhibitors; calcium antagonists; alpha blockers; beta blockers; thiamazole (methimazole) and analogous compounds; arginine; tetrahydrobiopterin; vitamins, in particular vitamin C and vitamin B6; niacine.

The compounds of the formula I and their pharmaceutically acceptable salts, optionally in combination with other pharmaceutically active compounds, can be administered to animals, preferably to mammals, and in particular to humans, as pharmaceuticals by themselves, in mixtures with one another or in the form of pharmaceutical preparations. A further subject of the present invention therefore also is a compound of the formula I as defined above and/or its pharmaceutically acceptable salts for use as a pharmaceutical. Another subject of the present invention is the use of a compound of the formula I and/or its pharmaceutically acceptable salts as transcription stimulating agent or upregulating agent of endothelial NO synthase, for example in conditions in which an increased expression of said enzyme or an increased NO level or the normalization of a decreased NO level in a patient is desired, and in particular its use in the treatment, i. e. the therapy and prevention, of the above-mentioned syndromes, as well as its use for preparing medicaments for these purposes, where this latter subject of the invention expressly also includes the use of the compounds of formula I and/or their pharmaceutically acceptable salts which are excluded by the proviso from the compounds defined above which are a subject of the invention as compounds per se. Likewise, all discussions herein regarding the compounds of formula I and their pharmaceutically acceptable salts which are the subject of the invention as compounds per se, for example processes for preparing them and details regarding their use as pharmaceuticals, are meant to apply to compounds of the invention excluded by the provisos.

Furthermore, a subject of the present invention are pharmaceutical preparations (or pharmaceutical compositions) which comprise an effective dose of at least one compound of the formula I and/or a pharmaceutically acceptable salt thereof as defined above, and a pharmaceutically acceptable carrier, i.e. one or more pharmaceutically acceptable carrier substances or vehicles and/or additives or excipients.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously, in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, among others, on the disease to be treated and on its severity.

The amount of a compound of the formula I and/or its pharmaceutically acceptable salts in the pharmaceutical preparations normally ranges from about 0.2 to about 800 mg, preferably from about 0.5 to about 500 mg, in particular from about 1 to about 200 mg, per dose, but depending on the type of the pharmaceutical preparation it may also be higher. The pharmaceutical preparations usually comprise from about 0.5 to about 90% by weight of the compounds of the formula I and/or their pharmaceutically acceptable salts. The production of the pharmaceutical preparations can be carried out in a manner known per se. To this end, one or more compounds of the formula I and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Soft gelatin capsules and suppositories can comprise, for example, fats, waxes, semisolid and liquid polyols, natural or hardened oils, etc. Suitable carrier substances or vehicles for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the compound or compounds of the invention and carrier substances, the pharmaceutical preparations can also contain additives such as, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the compound of the formula I to be administered and/or of a pharmaceutically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the use is for the therapy of a acute or chronic disease or prophylactic, or on whether other active compounds are administered in addition to compounds of the formula I. In general, a daily dose of from about 0.01 to about 100 mg/kg, preferably from about 0.1 to about 10 mg/kg, in particular from about 0.3 to about 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four, individual doses. In some cases, depending on the individual response, it may be necessary to deviate upwards or downwards from the given daily dose.

The compounds of the formula I can also be used for other purposes than those indicated in the foregoing. Non-limiting examples include diagnostic purposes, such as the use in the examination of cell or tissue samples, the use as biochemical tools and the use as intermediates for the preparation of further compounds, e.g. pharmaceutically active compounds.

EXAMPLES

HPLC Conditions

HPLC Method a

Column: Daicel Chiralpak AD, 250×4.6 mm, 10µ; eluent: acetonitrile/isopropanol (120/5)+0.1% diethylamine; flow rate: 1.0 ml/min HPLC Method b Column: Merck Purospher, 55×2 mm, 5µ; eluent A: water+0.05% trifluoroacetic acid, eluent B: acetonitrile; gradient: from 95% eluent A/5% eluent B to 5% eluent A/95% eluent B in 4 min, 5% eluent A/95% eluent B for 1.5 min; flow rate: 0.5 ml/min HPLC Method c Column: YMC J'Sphere ODS H80, 33×2 mm, 3µ; eluent A: water+0.05% trifluoroacetic acid, eluent B: acetonitrile; gradient: from 90% eluent A/10% eluent B to 5% eluent A/95% eluent B in 2.5 min, 5% eluent A/95% eluent B for 0.8 min; flow rate: 1.0 ml/min HPLC Method d Column: Daicel Chiralpak AD, 250×4.6 mm, 10µ; eluent: n-heptane/isopropanol (10/1); flow rate: 1.0 ml/min HPLC Method e Column: Merck Purospher, 55×2 mm, 3µ; eluent A: water+0.1% formic acid, eluent B: acetonitrile+0.08% formic acid; gradient: from 95% eluent A/5% eluent B to 5% eluent A/95% eluent B in 5 min, 5% eluent A/95% eluent B for 2 min; flow rate: 0.45 ml/min HPLC retention times (RT) are given in minutes.

General methods for the acylation of heteroaryl-condensed cycloalkenylamines

General acylation method A: 2.5 mmol of the respective amine were mixed with 550 mg of triethylamine and 5 ml of dioxane or tetrahydrofuran, and 2.5 mmol of the respective carboxylic acid chloride were added. The mixture was stirred at room temperature for 2 h and then poured onto a saturated sodium hydrogencarbonate solution. The mixture was extracted with ethyl acetate and the organic solution dried and concentrated. The residue was purified by preparative HPLC (RP18; acetonitrile/water+trifluoroacetic acid) or by silica gel flash chromatography (methylene chloride or methylene chloride/methanol).

General acylation method B: To 0.4 mmol of the respective carboxylic acid dissolved in 5 ml of tetrahydrofuran was added 144 mg (0.44 mmol) of O-((cyano(ethoxycarbonyl)methylene)amino)-N,N,N',N'-tetramethyluronium tetrafluoroborate (TOTU) in 1 ml of dimethylformamide and 114 mg (0.88 mmol) of ethyldiisopropylamine. After stirring at room temperature for 30 min, 0.37 mmol of the respective amine were added and the mixture was stirred for 12 h. The reaction mixture was poured onto a saturated sodium hydrogencarbonate solution, extracted with ethyl acetate and the organic solution dried and concentrated. The residue was purified by preparative HPLC (RP18, acetonitrile/water+trifluoroacetic acid) or by silica gel flash chromatography (methylene chloride or methylene chloride/methanol).

General acylation method C: 0.4 mmol of the respective amine and 75 µl (0.44 mmol) of ethyldiisopropylamine were dissolved in 1 ml of dimethylformamide and the solution was cooled to 0° C. Subsequently, a solution of 54 mg (0.44 mmol) of 4-dimethylaminopyridine in 0.5 ml of dimethylformamide, 0.44 mmol of the respective carboxylic acid and a solution of 59 mg (0.44 mmol) of 1-hydroxybenzotriazole in 0.5 ml of dimethylformamide were added and the mixture was stirred at 0° C. for 20 min. Then a solution of 68 mg (0.44 mmol) of N-(3-dimethylaminopropyl)-N'-ethylcarbodiimide in 0.5 ml of dimethylformamide was added and the mixture was stirred at room temperature for 12 h. The reaction mixture was filtered and the filter was rinsed twice with 10 ml of ethyl acetate. The solution was washed with 20 ml of a 5% sodium hydrogencarbonate solution and 20 ml of a 5% sodium chloride solution, and the organic phase was separated, dried over Chromabond XTR and evaporated to dryness. If desired, the product was purified via preparative HPLC (RP 18, acetonitrile/water+0.01% trifluoroacetic acid).

Example 1

N-(6,7-Dihydro-5H-[1]pyrindin-6-yl)-2,4-dimethyl-benzamide (enantiomer 1)

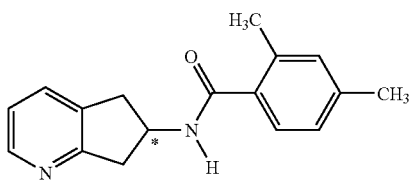

a) 7-Benzylidene-6,7-dihydro-5H-[1]pyrindine 15 g (0.125 mol) of 6,7-dihydro-5H-[1]pyrindine, 20.1 g (0.19 mol) of freshly distilled benzaldehyde and 24.5 g (0.24 mol) of acetic acid anhydride were heated under reflux for 24 h. The reaction mixture was evaporated, the residual oil dissolved in methylene chloride, the solution extracted with 1N NaOH solution, and the organic phase dried and evaporated. The residue was destilled under reduced pressure to give 19.3 g (75%) of the title compound.

Boiling point (0.013 mbar): 150° C. Melting point: 72° C.

b) 5,6-Dihydro-[1]pyrindin-7-one

19.3 g (0.09 mol) of the compound of step a were dissolved in 250 ml of dry methanol, cooled to −35° C. and ozonized for 3 h. 10.56 g (0.17 mol) of dimethylsulfide were added, and the reaction mixture was allowed to warm to room temperature overnight. Evaporation and subsequent distillation of the residual oil under reduced pressure gave 6.6 g of the title compound.

Boiling point (0.003 mbar): 150° C.

c) 5H-[1]Pyrindine-6,7-dione 6-oxime 6.6 g (49.6 mmol) of the compound of step b and 6.97 g (59.5 mmol) of isoamyl nitrite dissolved in 150 ml of methanol warmed to 45° C. and treated dropwise with 8 ml of concentrated hydrochloric acid. After stirring at 45° C. for 3 h, the mixture was cooled to 0° C. and the precipitated product collected by suction. Yield: 7.3 g (91%).

DC: Rf=0.2 (silica gel, methylene chloride/methanol (95/5)).

d) N-(6,7-Dihydro-5H-[1]pyrindin-6-yl)acetamide 18 g (0.11 mol) of the compound of step c were dissolved in 500 ml of acetic acid and 500 ml of acetic acid anhydride and hydrogenated for 20 h at a pressure of 2 bar over 5 g of palladium on barium sulfate. The reaction mixture was filtered and evaporated. The residue was dissolved in 1000 ml of ethanol, treated with 10.8 ml of perchloric acid and hydrogenated for 10 h at 50° C. and a pressure of 3.5 bar over 5 g of palladium on charcoal (10%). The resulting mixture was evaporated, the residue taken up in dilute NaOH solution and extracted with ethyl acetate. Evaporation of the combined organic phases and subsequent chromatography of the residue yielded racemic N-(6,7-dihydro-5H-[1]pyrindin-6-yl)acetamide.

DC: Rf=0.28 (silica gel, methylene chloride/methanol (9/1)).

The racemic acetamide was separated into the enantiomers by chromatography on a chiral phase (Chiralpak AD; eluent: acetonitrile/isopropanol (120/5)+0.1% diethylamine. The yield of enantiomer 1 of N-(6,7-dihydro-5H-[1]pyrindin-6-yl)acetamide was 1.89 g, the yield of enantiomer 2 of N-(6,7-dihydro-5H-[1]pyrindin-6-yl)acetamide was 1.53 g.

Enantiomer 1
HPLC: RT=6.40 min (method a).

Enantiomer 2
HPLC: RT=8.16 min (method a).

e) 6,7-Dihydro-5H-[1]pyrindin-6-ylamine (enantiomer 1 and enantiomer 2) The separated enantiomers of N-(6,7-dihydro-5H-[1]pyrindin-6-yl)acetamide were hydrolyzed by heating with 20 ml of 6N HCl in a sealed vessel to 150° C. for 4 h. Evaporation, treatment with an excess of 1N NaOH solution, extraction with ethyl acetate and drying and evaporation of the extracts yielded the two enantiomeric 6,7-dihydro-5H-[1]pyrindin-6-ylamines in a yield of 0.7 g and 0.8 g, respectively.

Enantiomer 1
MS: m/e=135 (M+H)$^+$. HPLC: RT=0.13 (method c).

Enantiomer 2
MS: m/e=135 (M+H)$^+$. HPLC: RT=0.13 (method c).

f) N-(6,7-Dihydro-5H-[1]pyrindin-6-yl)-2,4-dimethyl-benzamide (enantiomer 1) The title compound was prepared from chiral dihydro-5H-[1]pyrindin-6-ylamine of step e) according to general acylation method A.

MS: m/e=267 (M+H)$^+$. HPLC: RT=1.12 min (method c).

Example 2

N-(6,7-Dihydro-5H-[1]pyrindin-6-yl )-2,4-dimethyl-benzamide (enantiomer 2)

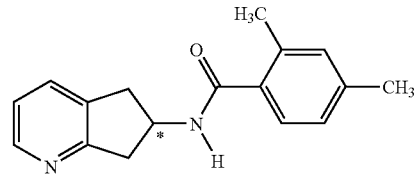

The title compound was prepared from chiral 6,7-dihydro-5H-[1]pyrindin-6-ylamine of Example 1, step e), according to general acylation method A.

MS: m/e=267 (M+H)$^+$. HPLC: RT=1.12 min (method c).

Example 3

N-(6,7-Dihydro-5H-[1]pyrindin-6-yl)-4-fluorobenzamide (enantiomer 1)

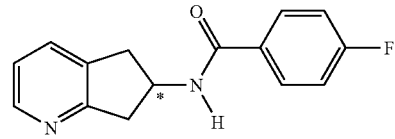

The title compound was prepared according to general acylation method A, starting from racemic 6,7-dihydro-5H-[1]pyrindin-6-ylamine which had been prepared from the racemic N-(6,7-dihydro-5H-[1]pyrindin-6-yl)acetamide of Example 1, step d, by hydrolysis analogously as described in Example 1, step e, and separation of the racemic N-(6,7-dihydro-5H-[1]pyrindin-6-yl)-4-fluorobenzamide by preparative chromatography on a chiral phase (Chiralpak AD; eluent: heptane/isopropanol (10/1).

MS: m/e=257 (M+H)$^+$. HPLC: RT=15.66 min (method d).

Example 4

N-(6,7-Dihydro-5H-[1]pyrindin-6-yl)-4-fluorobenzamide (enantiomer 2)

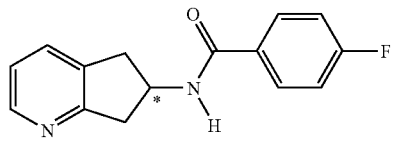

The title compound was prepared as described in Example 3 by separation of N-(6,7-dihydro-5H-[1]pyrindin-6-yl)-4-fluorobenzamide.
MS: m/e=257 (M+H)$^+$. HPLC: RT=14.96 min (method d)

Example 5

N-(6,7-Dihydro-5H-[1]pyrindin-6-yl)-2,6-dimethylnicotinamide (enantiomer 1)

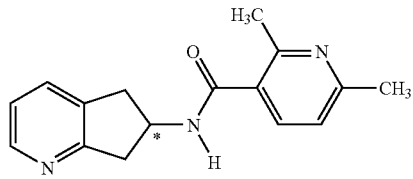

The title compound was prepared from chiral 6,7-dihydro-5H-[1]pyrindin-6-ylamine of Example 1, step e, according to general acylation method A.
MS: m/e=268 (M+H)$^+$. HPLC: RT=0.15 min (method c).

Example 6

N-(6,7-Dihydro-5H-[1]pyrindin-6-yl)-6-methoxynicotinamide (enantiomer 1)

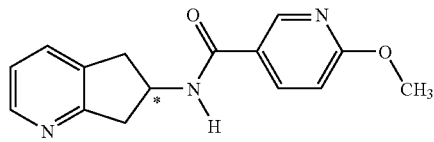

The title compound was prepared from chiral 6,7-dihydro-5H-[1]pyrindin-6-ylamine of Example 1, step e, according to general acylation method A.
MS: m/e=270 (M+H)$^+$. HPLC: RT=0.43 min (method c).

Example 7

2-Methyl-3H-benzimidazole-5-carboxylic acid (6,7-dihydro-5H-[1]pyrindin-6-yl)amide (enantiomer 1)

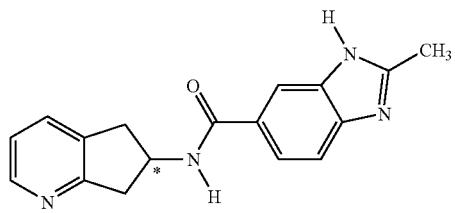

The title compound was prepared from chiral 6,7-dihydro-5H-[1]pyrindin-6-ylamine of Example 1, step e, according to general acylation method A.
MS: m/e=293 (M+H)$^+$. HPLC: RT=0.17 min (method c).

Example 8

N-(6,7-Dihydro-5H-[1]pyrindin-6-yl)-6-methoxymethyinicotinamide (enantiomer 1)

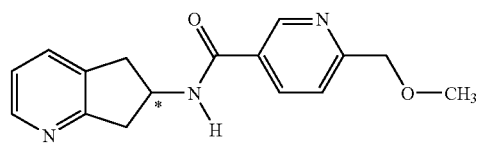

The title compound was prepared from chiral 6,7-dihydro-5H-[1]pyrindin-6-ylamine of Example 1, step e, according to general acylation method B.
MS: m/e=284 (M+H)$^+$. HPLC: RT=1.77 min (method b).

Example 9

2,2-Difluorobenzo[1,3]dioxole-5-carboxylic acid (6,7-dihydro-5H-[1]pyrindin-6-yl)amide (enantiomer 1), trifluoroacetic acid salt

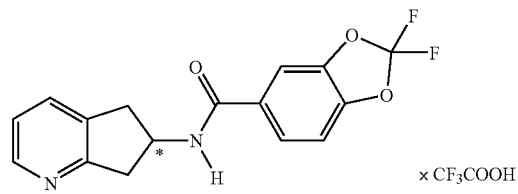

The title compound was prepared from chiral 6,7-dihydro-5H-[1]pyrindin-6-ylamine of Example 1, step e, according to general acylation method B.
MS: m/e=319 (M+H)$^+$. HPLC: RT=1.60 min (method c).

Example 10

4-Chloro-N-(6,7-dihydro-5H-[1]pyrindin-6-yl)benzamide (enantiomer 1), trifluoroacetic acid salt

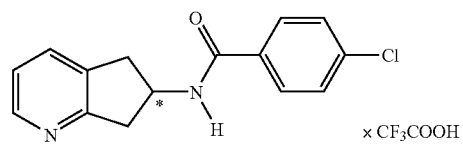

The title compound was prepared from chiral 6,7-dihydro-5H-[1]pyrindin-6-ylamine of Example 1, step e, according to general acylation method A.
MS: m/e=273 (M+H)$^+$. DC: Rf=0.29 (silica gel, methylene chloride/methanol (95/5)).

Example 11

2,4-Dimethyl-N-(6,7,8,9-tetrahydro-5H-cyclohepta[b]pyridin-8-yl)benzamide

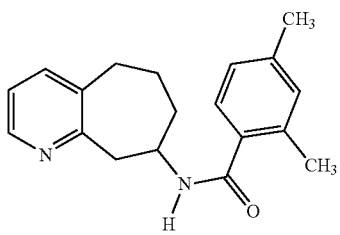

a) 9-Benzylidene-6,7,8,9-tetrahydro-5H-cyclohepta[b]pyridine

The title compound was prepared from 6,7,8,9-tetrahydro-5H-cyclohepta[b]pyridine analogously as described in Example 1, step a. The raw material was purified by silica gel chromatography using methylene chloride as eluent.

MS: m/e=236 (M+H)$^+$. DC: Rf=0.47 (silica gel, n-heptane/ethyl acetate (3/2)).

b) 5,6,7,8-Tetrahydrocyclohepta[b]pyridin-9-one

The title compound was prepared from the compound of step a analogously as described in Example 1, step b. The raw material was purified by silica gel chromatography using methylene chloride/methanol (98/2) as eluent.

MS: m/e=162 (M+H)$^+$. DC: Rf=0.72 (silica gel, methylene chloride/methanol (98/2)).

c) 6,7-Dihydro-5H-cyclohepta[b]pyridine-8,9-dione 8-oxime 6.7 g (41.6 mmol) of the compound of step b were dissolved in 300 ml of diethyl ether and treated with 10 ml of a saturated solution of hydrogen chloride in diethyl ether. To the resulting slurry were added 5.38 g (45.8 mmol) of isoamyl nitrite in 500 ml of tetrahydrofuran and once more 10 ml of a saturated solution of hydrogen chloride in diethyl ether. The mixture was refluxed for 3 h, cooled in an ice bath and the. precipitated product isolated by suction: Yield 7.9 g (100%).

MS: m/e=191 (M+H)$^+$. Rf=0.20 (silica gel, methylene chloride/methanol (98/2)).

d) 6,7,8,9-Tetrahydro-5H-cyclohepta[b]pyridin-8-ylamine

The title compound was prepared from the compound of step c analogously as described in Example 1, steps d and e. The raw material was purified by silica gel chromatography using methylene chloride/methanol (98/2) as eluent.

MS: m/e=163 (M+H)+. Rf=0.09 (silica gel, methylene chloride/methanol (7/3)).

e) 2,4-Dimethyl-N-(6,7,8,9-tetrahydro-5H-cyclohepta[b]pyridin-8-yl)benzamide

The title compound was prepared from the compound of step d according to general acylation method A.

MS: m/e=295 (M+H)$^+$. HPLC: RT=3.68 min (method b).

Example 12

3-Amino-5-methylpyrazine-2-carboxylic acid (5,6-dihydro4H-cyclopenta[b]thiophen-5-yl)amide

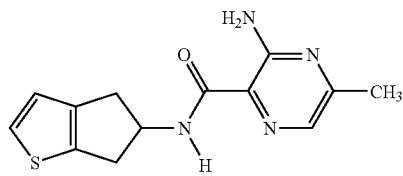

a) 5,6-Dihydro-4H-cyclopenta[b]thiophen-5-ylamine hydrochloride 2.289 g (13.61 mmol) of 5,6-dihydro-4H-cyclopenta[b]thiophene-5-carboxylic acid (U.S. Pat. No. 5,753,662) were dissolved in 25 ml of acetonitrile, 4.120 g (14.97 mmol) of diphenylphosphoryl azide and 1.515 g (14.97 mmol) of triethylamine were added, and the mixture was stirred at room temperature for 2.5 h. Then 11.51 ml (168.4 mmol) of allyl alcohol were added and the reaction mixture was heated at 50° C. overnight. The solvent was evaporated and the residue taken up in ethyl acetate and extracted with a 10% sodium hydrogencarbonate solution. The organic phase was separated, dried and evaporated to dryness. The residue was taken up in 200 ml of methylene chloride and added to a mixture of 2.60 ml (16.32 mmol) of triethylsilane, 320 µl (2.312 mmol) of triethylamine and 153 mg of palladium acetate. After stirring at room temperature for 3 h, the solvent was evaporated, the residue taken up in ethyl acetate and extracted with a 10% sodium hydrogencarbonate solution. The organic phase was separated and extracted with diluted hydrochloric acid. The combined hydrochloric acid phases were freeze-dried to yield 1.44 g of the title compound which was used in the acylation step without further purification.

b) 3-Amino-5-methyl pyrazine-2-carboxylic acid (5,6-dihydro-4H-cyclopenta[b]thiophen-5-yl)amide The title compound was prepared from 5,6-dihydro-4H-cyclopenta[b]thiophen-5-ylamine hydrochloride of step a) according to general acylation method C.

MS: m/e=275 (M+H)$^+$. HPLC: RT=3.62 min (method e).

The following examples 13 to 31 were prepared from 5,6-dihydro-4H-cyclopenta[b]thiophen-5-ylamine hydrochloride of Example 12, step a) according to general acylation method C.

Example 13

N-(5,6-Dihydro-4H-cyclopenta[b]thiophen-5-yl)-2,6-dimethylnicotinamide, trifluoroacetic acid salt

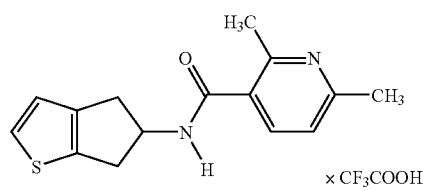

MS: m/e=273 (M+H)$^+$. HPLC: RT=1.80 Min (method e).

Example 14

N-(5,6-Dihydro-4 H-cyclopenta[b]thiophen-5-yl)-6-methoxynicotinamide

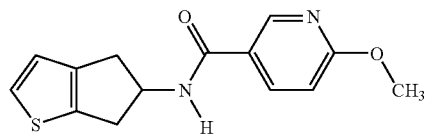

MS: m/e=275 (M+H)⁺. HPLC: RT=3.30 min (method e).

Example 15

2-Methyl-3H-benzimidazole-5-carboxylic acid (5,6-dihydro-4H-cyclopenta[b]thiophen-5-yl)amide, trifluoroacetic acid salt

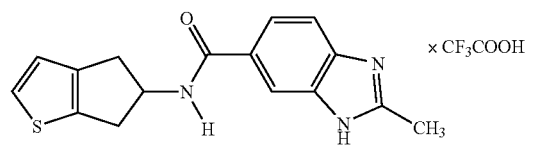

MS: m/e=298 (M+H)⁺. HPLC: RT=1.93 min (method e).

Example 16

5-Methyl-1-phenyl-1H-pyrazole-4-carboxylic acid (5,6-dihydro-4H-cyclopenta[b]thiophen-5-yl)amide

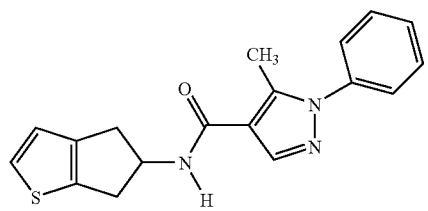

MS: m/e=324 (M+H)⁺. HPLC: RT=3.67 min (method e).

Example 17

1-Phenyl-5-trifluoromethyl-1H-pyrazole-4-carboxylic acid (5,6-dihydro-4H-cyclopenta[b]thiophen-5-yl)amide

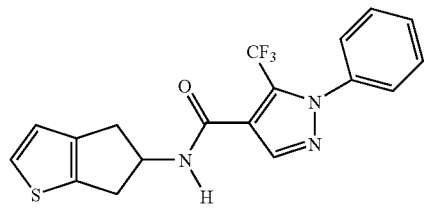

MS: m/e=378 (M+H)⁺. HPLC: RT=4.02 min (method e).

Example 18

2,5-Dimethyl-1-pyridin-4-ylmethyl-1H-pyrrole-3-carboxylic acid (5,6-dihydro-4H-cyclopenta[b]thiophen-5-yl)amide, trifluoroacetic acid salt

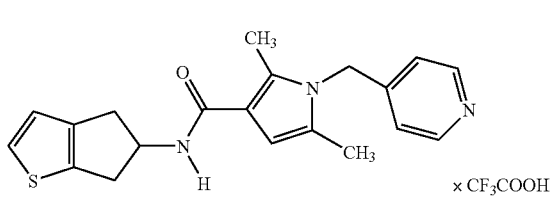

MS: m/e=352 (M+H)⁺. HPLC: RT=2.37 min (method e).

Example 19

2,4-Dimethylthiazole-5-carboxylic acid (5,6-dihydro-4H-cyclopenta[b]thiophen-5-yl)amide

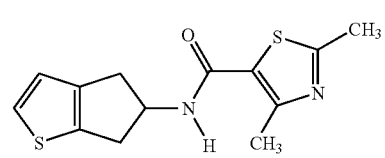

MS: m/e=279 (M+H)⁺. HPLC: RT=3.12 min (method e).

Example 20

1,3-Dimethyl-1H-pyrazole-4-carboxylic acid (5,6-dihydro-4H-cyclopenta[b]thiophen-5-yl)amide

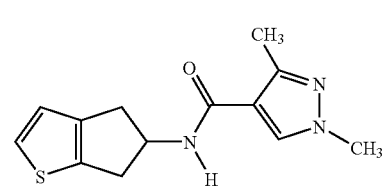

MS: m/e=262 (M+H)⁺. RT=2.79 min (method e).

Example 21

2-Amino-N-(5,6-dihydro-4H-cyclopenta[b]thiophen-5-yl)nicotinamide, trifluoroacetic acid salt

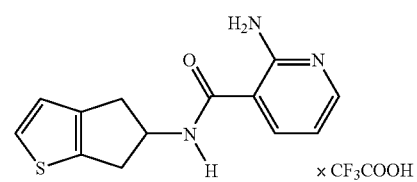

MS: m/e=260 (M+H)⁺. HPLC: RT=1.85 min (method e).

Example 22

N-(5,6-Dihydro-4H-cyclopenta[b]thiophen-5-yl)-6-methylnicotinamide, trifluoroacetic acid salt

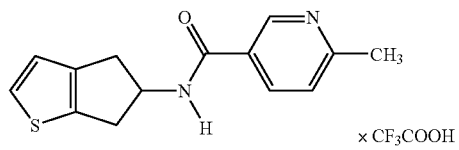

MS: m/e=259 (M+H)$^+$. HPLC: RT=2.17 min (method e).

Example 23

2-Chloro-N-(5,6-dihydro-4H-cyclopenta[b]thiophen-5-yl)-6-methylnicotinamide

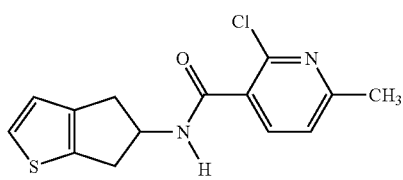

MS: m/e=293 (M+H)$^+$. HPLC: RT=3.20 min (method e).

Example 24

N-(5,6-Dihydro4H-cyclopenta[b]thiophen-5-yl)-6-methoxymethylnicotinamide, trifluoroacetic acid salt

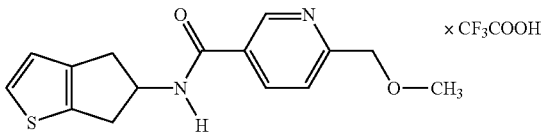

MS: m/e=289 (M+H)$^+$. HPLC: RT=2.84 min (method e).

Example 25

3-Aminopyrazine-2-carboxylic acid (5,6-dihydro-4H-cyclopenta[b]thiophen-5-yl)amide

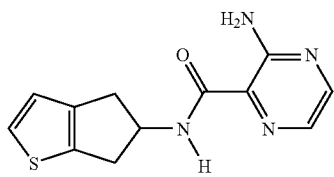

MS: m/e=261 (M+H)$^+$. HPLC: RT=3.42 min (method e).

Example 26

2,3-Dichloro-N-(5,6-dihydro-4H-cyclopenta[b]thiophen-5-yl)benzamide

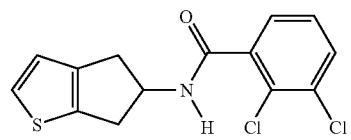

MS: m/e=312 (M+H)$^+$. HPLC: RT=3.90 min (method e).

Example 27

N-(5,6-Dihydro-4H-cyclopenta[b]thiophen-5-yl)-2,4-dimethylbenzamide

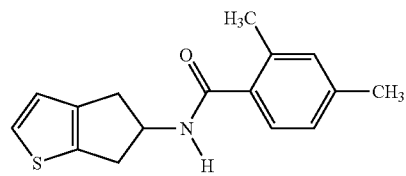

MS: m/e=272 (M+H)$^+$. HPLC: RT=3.87 min (method e).

Example 28

N-(5,6-Dihydro-4H-cyclopenta[b]thiophen-5-yl)-2,4-difluorobenzamide

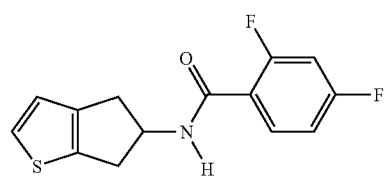

MS: m/e=280 (M+H)$^+$. HPLC: RT=3.79 min (method e).

Example 29

N-(5,6-Dihydro-4H-cyclopenta[b]thiophen-5-yl)-3-methylsulfonylaminobenzamide

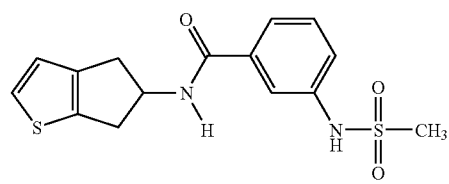

MS: m/e=337 (M+H)$^+$. HPLC: RT=3.12 min (method e).

Example 30

N-(5,6-Dihydro-4H-cyclopenta[b]thiophen-5-yl)-6-(morpholin-4-yl)nicotinamide, trifluoroacetic acid salt

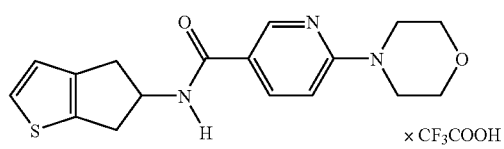

MS: m/e=330 (M+H)$^+$. HPLC: RT=2.73 min (method e).

Example 31

N-(5,6-Dihydro-4H-cyclopenta[b]thiophen-5-yl)-3-(morpholin-4-yl)benzamide

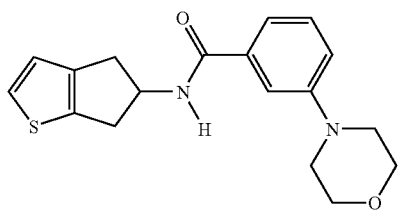

MS: m/e=329 (M+H)$^+$. HPLC: RT=3.43 min (method e).

Determination of Activation of eNOS Transcription

Activation of eNOS transcription was determined as described in detail in Li et al., "Activation of protein kinase C alpha and/or epsilon enhances transcription of the human endothelial nitric oxide synthase gene", Mol. Pharmacol. 53 (1998) 630, the content of which is incorporated herein by reference.

Briefly, a 3.5 kB long fragment 5' of the starting codon of the eNOS gene was cloned, sequenced and cloned in firefly luciferase expression plasmids to monitor activation of the eNOS promoter by reporter gene activity. A human endothelial cell line stable transfected and expressing this promoter-reporter construct was used for compound testing. Cells were incubated for 18 h with compounds.

All compounds were dissolved in sterile dimethyl sulfoxide (DMSO). A final concentration of 0.5% DMSO in complete medium was allowed. Induction of reporter gene expression in these cells was measured using a standard luciferase assay system (Promega, Cat. No E150) according to the manufacturer's instructions. Luciferase induction in cells incubated with compounds were compared to those incubated with solvent alone. The ratio of both activities (transcription induction ratio, TIR) was plotted as a function of compound concentration,. Typically, TIR values started at low concentrations at a ratio of 1, indicating no compound effect, and extended up to a maximum TIR value TIR(max) which indicates the increase of the eNOS transcription. $EC_{50}$ values of transcription induction ratios as a function of compound concentration were determined graphically.

The effect of compounds on eNOS-transcription was confirmed in a second assay based on eNOS protein detection. Primary human umbilical vein cord endothelial cells (HUVEC) were isolated and cultivated according to standard procedures. Confluent cells were incubated with compounds for 18 h and the effect on eNOS protein expression determined by a quantitative Western blotting procedure. After compound incubation, HUVEC were lysed in ice-cold lysis buffer containing 10 mM Tris-HCl, pH 8.0, 1% SDS and protease inhibitors. The lysate was subjected to a standard denaturating polyacrylamide gel electrophoresis and blotted to nitrocellulose membranes. Using a specific primary monoclonal antibody (Transduction Laboratories, UK) and alkaline phosphatase labelled secondary antibody (Jackson Labs), a specific eNOS protein band was visualized and quantified based on a chemifluorescence detection method.

The results are shown in the Table below.

| Compound of example no. | $EC_{50}$ (µM) |
|---|---|
| 1 | 0.079 |
| 2 | 1.1 |
| 3 | 14 |
| 4 | 3.4 |
| 5 | 3.3 |
| 6 | 12 |
| 7 | 23 |
| 8 | 30 |
| 9 | 0.93 |
| 10 | 0.80 |
| 11 | 0.064 |
| 12 | 11 |
| 13 | 0.62 |
| 14 | 2.4 |
| 15 | 3.1 |
| 16 | 0.20 |
| 17 | 0.35 |
| 18 | 3.3 |
| 19 | 20 |
| 20 | 9.8 |
| 21 | 4.8 |
| 22 | 1.6 |
| 23 | 0.80 |
| 24 | 125 |
| 25 | 18 |
| 26 | 1.5 |
| 27 | <0.1 |
| 28 | 0.76 |
| 29 | 2.3 |
| 30 | 11 |
| 31 | 3.3 |

The effect of the compounds of the invention can also be investigated in the following animal models (animal experiments are performed in accordance to the German animal protection law and to the guidelines for the use of experimental animals as given by the Guide for the Care and Use of Laboratory Animals of the US National Institutes of Health).

Animals and Treatment (Experiments A–C)

ApoE and eNOS deficient mice (C57BL/6J background, Jackson Laboratory, Bar Harbor, Me.) are used. All animals are 10 to 12 weeks of age and weigh 22 to 28 g. Three days before surgery mice are divided into 4 groups (apoE control, n=10 to 12; apoE with test compounds, n=10 to 12; eNOS control, n=10 to 12; eNOS with test compounds, n=10 to 12) and receive either a standard rodent chow (containing 4% fat and 0.001% cholesterol; in the following designated as placebo group) or a standard rodent chow+test compound (10 or 30 mg/kg/d p.o.).

A. Anti-hypertensive Effect in ApoE Knockout Mice

Blood-pressure is determined in conscious mice using a computerized tail-cuff system (Visitech Systems, Apex, Nc). After treatment of ApoE deficient mice and eNOS deficient mice with the test compounds the blood pressure is compared to the results obtained with a placebo treatment.

B. Inhibition of Neointima Formation and Atherogenesis (Femoral Artery Cuff)

After 3 day treatment of ApoE deficient mice with the respective compound, (10 mg/kg/d pressed in chow), animals are anesthetized with an intraperitoneal injection of pentobarbital (60 mg/kg) followed by an intramuscular injection of xylazin (2 mg/kg) and a cuff is placed around the femoral artery as described in Moroi et al.(J. Clin. Invest. 101 (1998) 1225, the content of which is incorporated by reference). Briefly, the left femoral artery is dissected. A non-occlusive 2.0 mm polyethylene cuff made of PE-50 tubing (inner diameter 0.56 mm, outer diameter 0.965 mm, Becton Dickinson, Mountain View, Calif.) is placed around the artery and tied in place with two 7-0 sutures. The right femoral artery is isolated from the surrounding tissues but a cuff is not placed. Treatment with the respective compound is continued for 14 days after surgery. Then the animals are sacrificed. The aorta are taken for determination of vascular eNOS expressions by quantitative western blotting. Both femoral arteries are harvested, fixed in formalin and embedded in paraffin. 20 cross sections (10 μm) are cut from the cuffed portion of the left femoral artery and from the corresponding segment of the right artery. Sections are subjected to standard hematoxylin and eosin staining. Morphometric analyses are performed using an image analysis computer program (LeicaQWin, Leica Imaging Systems, Cambridge, GB). For each cross section the area of the lumen, the neointima and the media are determined. To this end, the neointima is defined as the area between the lumen and the internal elastic lamina and the media is defined as the area between the internal and the external elastic lamina. The ratio between the area of the neointima and the area of the media is expressed as the neointima/media ratio. The results obtained in the compound group are compared to those obtained in the placebo group.

C. Prevention of Atherosclerotic Plaque Formation in Chronic Treatment

ApoE deficient mice are treated for 16 weeks with the respective compound pressed in chow and finally sacrificed. Aortas are removed from each mouse, fixed in formalin and embedded in paraffin. Plaque formation is measured via lipid lesions formation in the aortas (from aortic arch to diaphragm) and is analyzed by oil red O staining. For quantifying the effect of the respective compound on vascular eNOS expression the femoral arteries are used in this experiment. The results obtained in the compound group are compared to those obtained in the placebo group.

D. Improvement of Coronary Function in Diseased ApoE Deficient Mice

Old Male wild-type C57BL/6J mice (Charles River Wiga GmbH, Sulzfeld), and apoE deficient mice (C57BL/6J background, Jackson Laboratory, Bar Harbor, Me.) 6 month of age and weighing 28 to 36 g are used in the experiments. Mice are divided into 3 groups (C57BL/6, n=8; apoE control, n=8; apoE with respective compound, n=8) and receive for 8 weeks either a standard rodent chow (containing 4% fat and 0.001% cholesterol) or a standard rodent chow+respective compound (30 mg/kg/d p.o.). Mice are anesthetized with sodium pentobarbitone (100 mg/kg i.p.), and the hearts are rapidly excised and placed into ice-cold perfusion buffer. The aorta is cannulated and connected to a perfusion apparatus (Hugo Sachs Electronics, Freiburg, Germany) which is started immediately at a constant perfusion pressure of 60 mm Hg. Hearts are perfused in a retrograde fashion with modified Krebs bicarbonate buffer, equilibrated with 95% $O_2$ and 5% $CO_2$ and maintained at 37.5° C. A beveled small tube (PE 50) is passed through a pulmonary vein into the left ventricle and pulled through the ventricular wall, anchored in the apex by a fluted end, and connected to a tip-micromanometer (Millar 1.4 French). The left atrium is cannulated through the same pulmonary vein and the heart switched to the working mode with a constant preload pressure of 10 mm Hg and an afterload pressure of 60 mm Hg. Aortic outflow and atrial inflow are continuously measured using ultrasonic flow probes (HSE/Transonic Systems Inc.). Coronary flow is calculated as the difference between atrial flow and aortic flow. All hemodynamic data are digitized at a sampling rate of 1000 Hz and recorded with a PC using spezialized software (HEM, Notocord).

Hearts are allowed to stabilize for 30 min. All functional hemodynamic data are measured during steady state, and during volume- and pressure loading. Left ventricular function curves are constructed by varying pre-load pressure. For acquisition of preload curves, afterload is set at 60 mm Hg and preload is adjusted in 5 mm Hg steps over a range of 5 to 25 mm Hg. Hearts are allowed to stabilize at baseline conditions between pressure- and volume-loading.

What is claimed is:

1. A compound of the formula I,

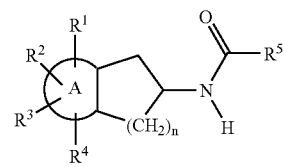

wherein:

the ring A, which comprises the two carbon atoms common to the ring A and the cycloalkenyl ring in formula I, is an aromatic 5-membered or 6-membered ring containing 1 or 2 nitrogen atoms as ring heteroatoms, or ring A is an aromatic 5-membered ring containing 1 ring heteroatom which is an oxygen atom or a sulfur atom or containing 2 ring heteroatoms one of which is a nitrogen atom and the other of which is an oxygen atom or a sulfur atom;

$R^1$ and $R^4$ are independently from each other:

H;

unsubstituted or substituted $C_1$–$C_{10}$-alkyl, unsubstituted or substituted $C_2$–$C_{10}$-alkenyl or unsubstituted or substituted $C_2$–$C_{10}$-alkynyl, the substituents of which are selected from the group consisting of F, OH, $C_1$–$C_8$-alkoxy, $C_1$–$C_8$-alkylmercapto, —CN, $COOR^6$, $CONR^7R^8$, and unsubstituted or substituted phenyl or unsubstituted or substituted heteroaryl where the substituents of the phenyl and heteroaryl group are selected from the group consisting of halogen, —CN, $C_1$–$C_3$-alkyl, $C_1$–$C_3$-alkoxy and $CF_3$;

unsubstituted or substituted phenyl or heteroaryl the substituents of which are selected from the group consisting of halogen, —CN, $C_1$–$C_3$-alkyl, $C_1$–$C_3$-alkoxy and $CF_3$;

COR$^9$; CONR$^{10}$R$^{11}$; COOR$^{12}$; CF$_3$; halogen; —CN; NR$^{13}$R$^{14}$; OR$^{15}$; S(O)$_m$R$^{16}$; SO$_2$NR$^{17}$R$^{18}$; or NO$_2$;

provided that, when R$^1$ or R$^4$, in each case, is bonded to a ring nitrogen atom, then R$^1$ or R$^4$, in each case, is other than halogen, —CN or NO$_2$;

R$^2$ and R$^3$ are independently from each other:

H; halogen;

unsubstituted or substituted C$_1$–C$_{10}$-alkyl the substituents of which are selected from the group consisting of OH, phenyl, and heteroaryl;

OH; C$_1$–C$_{10}$-alkoxy; phenoxy; S(O)$_m$R$^{19}$; CF$_3$; —CN; NO$_2$; C$_1$–C$_{10}$-alkylamino; di(C$_1$–C$_{10}$-alkyl)amino; (C$_1$–C$_6$-alkyl)—CONH—;

unsubstituted or substituted phenyl-CONH— or unsubstituted or substituted phenyl-SO$_2$—O— the substituents of which are selected from the group consisting of halogen, —CN, methyl and methoxy;

C$_1$–C$_6$-alkyl-SO$_2$—O—;

unsubstituted or substituted (C$_1$–C$_6$-alkyl)—CO— the substituents of which are selected from the group consisting of F, di(C$_1$–C$_3$-alkyl)amino, pyrrolidinyl and piperidinyl; or phenyl-CO— the phenyl part of which is unsubstituted or substituted by substituents selected from the group consisting of C$_1$–C$_3$-alkyl, halogen and methoxy;

provided that, when R$^2$ or R$^3$, in each case, is bonded to a ring nitrogen atom, then R$^2$ or R$^3$, in each case, is other than halogen, —CN or NO$_2$;

provided that, when A is a 6-membered aromatic ring, then two or three of the groups R$^1$, R$^2$, R$^3$ and R$^4$ are present and are bonded to the carbon atoms in the ring A which are not shared with the cycloalkenyl ring of formula I, and provided that when A is a 5-membered aromatic ring, then one, two or three of the groups R$^1$, R$^2$, R$^3$ and R$^4$ are present and are bonded to the carbon atoms in the ring A which are not shared with the cycloalkenyl ring of formula I, and, when ring A is a pyrrole, pyrazole or imidazole ring, to one ring nitrogen;

R$^5$ is a group Ar or a group Hetar each of which is unsubstituted or carries one or more identical or different substituents selected from the group consisting of:

halogen; —CN; NH$_2$;

unsubstituted or substituted C$_1$–C$_{10}$-alkyl, unsubstituted or substituted C$_2$–C$_{10}$-alkenyl, unsubstituted or substituted C$_2$–C$_{10}$-alkynyl, unsubstituted or substituted C$_1$–C$_{10}$-alkoxy, unsubstituted or substituted C$_1$–C$_{10}$-alkylamino and unsubstituted or substituted di(C$_1$–C$_{10}$-alkyl)amino, the substituents of each of which are selected from the group consisting of F, OH, C$_1$–C$_8$-alkoxy, aryloxy, C$_1$–C$_8$-alkylmercapto, NH$_2$, C$_1$–C$_8$-alkylamino and di(C$_1$–C$_8$-alkyl)amino;

C$_3$–C$_5$-alkandiyl; phenyl; heteroaryl; aryl-substituted or heteroaryl-substituted C$_1$–C$_4$-alkyl; CF$_3$; NO$_2$; OH; phenoxy; benzyloxy; (C$_1$–C$_{10}$-alkyl)—COO—; S(O)$_m$R$^{20}$; SH; phenylamino; benzylamino; (C$_1$–C$_{10}$-alkyl)—CONH—; (C$_1$–C$_{10}$-alkyl)—CO—N(C$_1$–C$_4$-alkyl)—; phenyl-CONH—; phenyl-CO—N(C$_1$–C$_4$-alkyl)—; heteroaryl-CONH-; heteroaryl-CO—N(C$_1$–C$_4$-alkyl)—; (C$_1$–C$_{10}$-alkyl)—CO—; phenyl-CO—; heteroaryl-CO—; CF$_3$—CO—; —OCH$_2$O—; —OCF$_2$O—; —OCH$_2$CH$_2$O—; —CH$_2$CH$_2$O—; COOR$^{21}$; CONR$^{22}$R$^{23}$; C(NH)—NH$_2$; SO$_2$NR$^{24}$R$^{25}$; R$^{26}$SO$_2$NH—; R$^{27}$SO$_2$N(C$_1$–C$_6$-alkyl)—; or a residue of a saturated or at least monounsaturated aliphatic, monocyclic 5-membered to 7-membered heterocycle containing 1, 2 or 3 heteroatoms selected from the group consisting of N, O and S, which heterocycle can be substituted by one or more substituents selected from the group consisting of halogen, C$_1$–C$_3$-alkyl, C$_1$–C$_3$-alkoxy, OH, oxo and CF$_3$, where said heterocycle can optionally be condensed to the said group Ar or the said group Hetar;

wherein all aryl, heteroaryl, phenyl, aryl-containing, heteroaryl-containing and phenyl-containing groups, which are optionally present in the said substituents of the said group Ar or the said group Hetar, can be substituted by one or more substituents selected from the group consisting of halogen, —CN, C$_1$–C$_3$-alkyl, OH, C$_1$–C$_3$-alkoxy, and CF$_3$;

R$^6$ is

H;

C$_1$–C$_{10}$-alkyl which can be substituted by one or more substituents selected from the group consisting of F, C$_1$–C$_8$-alkoxy and di(C$_1$–C$_8$-alkyl)amino;

aryl-(C$_1$–C$_4$-alkyl)— or heteroaryl-(C$_1$–C$_4$-alkyl)— each of which can be substituted by one or more substituents selected from the group consisting of halogen, C$_1$–C$_4$-alkyl, C$_1$–C$_4$-alkoxy and di(C$_1$–C$_6$-alkyl)amino;

R$^7$ is

H;

C$_1$–C$_{10}$-alkyl which can be substituted by one or more substituents selected from the group consisting of F, C$_1$–C$_8$-alkoxy, di(C$_1$–C$_8$-alkyl)amino and phenyl;

phenyl; indanyl; or heteroaryl;

wherein each of the aromatic groups can be unsubstituted or carry one or more substituents selected from the group consisting of halogen, —CN, C$_1$–C$_3$-alkyl, C$_1$–C$_3$-alkoxy and CF$_3$;

R$^8$ is H or C$_1$–C$_{10}$-alkyl;

R$^9$ is

C$_1$–C$_{10}$-alkyl which can be substituted by one or more substituents selected from the group consisting of F, C$_1$–C$_4$-alkoxy and di(C$_1$–C$_3$-alkyl)amino; or unsubstituted or substituted phenyl or unsubstituted or substituted heteroaryl the substituents of each of which are selected from the group consisting of C$_1$–C$_3$-alkyl, C$_1$–C$_3$-alkoxy, halogen, —CN and CF$_3$;

R$^{10}$, independently from R$^7$, is R$^7$;

R$^{11}$, independently from R$^8$, is R$^8$;

R$^{12}$, independently from R$^6$, is R$^6$;

R$^{13}$ is

H; C$_1$–C$_6$-alkyl;

unsubstituted or substituted phenyl, unsubstituted or substituted benzyl, unsubstituted or substituted heteroaryl, unsubstituted or substituted (C$_1$–C$_6$-alkyl)—CO—, unsubstituted or substituted phenyl-CO—, or unsubstituted or substituted heteroaryl-CO—, the substituents of each of which are selected from the group consisting of halogen, —CN, C$_1$–C$_3$-alkyl, C$_1$–C$_3$-alkoxy and CF$_3$, wherein one or more of these substituents can be present;

R$^{14}$, independently from R$^{13}$, is R$^{13}$;

R$^{15}$ is

H; C$_1$–C$_{10}$-alkyl; (C$_1$–C$_3$-alkoxy)—C$_1$–C$_3$-alkyl-; or substituted or unsubstituted benzyl, substituted or unsubstituted phenyl or substituted or unsubstituted heteroaryl, the substituents of each of which are selected from the group consisting of halogen, —CN, C$_1$–C$_3$-alkyl, C$_1$–C$_3$-alkoxy and CF$_3$, wherein one or more of these substituents can be present;

43

$R^{16}$ is $C_1$–$C_{10}$-alkyl which can be substituted by one or more substituents selected from the group consisting of F, OH, $C_1$–$C_8$-alkoxy, aryloxy, $C_1$–$C_8$-alkylmercapto, $C_1$–$C_8$-alkylamino and di($C_1$–$C_8$-alkyl)amino;

$CF_3$; or substituted or unsubstituted phenyl or substituted or unsubstituted heteroaryl, the substituents of which are selected from the group consisting of halogen, —CN, $C_1$–$C_3$-alkyl, $C_1$–$C_3$-alkoxy and $CF_3$, wherein one or more of these substituents can be present;

$R^{17}$, independently from $R^7$, is $R^7$;
$R^{18}$, independently from $R^8$, is $R^8$;
$R^{19}$, independently from $R^{16}$, is $R^{16}$;
$R^{20}$, independently from $R^{16}$, is $R^{16}$;
$R^{21}$, independently from $R^6$, is $R^6$;
$R^{22}$, independently from $R^7$, is $R^7$;
$R^{23}$, independently from $R^8$, is $R^8$;
$R^{24}$, independently from $R^7$, is $R^7$;
$R^{25}$, independently from $R^8$, $R^8$;
$R^{26}$, independently from $R^{16}$, is $R^{16}$;
$R^{27}$, independently from $R^{16}$, is $R^{16}$;

heteroaryl is a residue of a 5-membered to 10-membered, aromatic, monocyclic or bicyclic heterocycle containing one or more heteroatoms selected from the group consisting of N, O and S;

the group Hetar is a residue of a 5-membered to 10-membered, aromatic, monocyclic or bicyclic heterocycle containing one or more heteroatoms selected from the group consisting of N, O and S;

aryl is phenyl, naphth-1-yl or naphth-2-yl;
the group Ar is phenyl, naphth-1-yl or naphth-2-yl;
m is 0, 1 or 2;
n is 1, 2 or 3; or a stereoisomer or a mixture of stereoisomers of such compound in any ratio, or a pharmaceutically acceptable salt of such compound, stereoisomer or mixture; provided that when the compound of the formula I is the compound of the formula

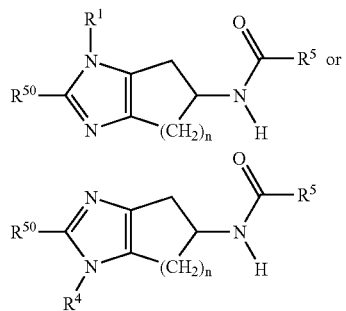

then $R^{50}$ is other than hydrogen, unsubstituted $C_1$–$C_6$-alkyl, $C_1$–$C_6$-alkoxy, unsubstituted $C_1$–$C_6$-alkylthio, halogen, —CN, $CF_3$, OH, amino, $C_1$–$C_6$-alkylamino or di($C_1$–$C_6$-alkyl)amino;

and provided that when the compound of formula I is the compound of the formula

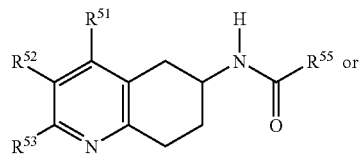

44

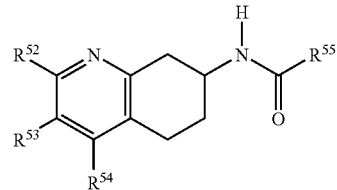

then $R^{51}$, $R^{52}$, $R^{53}$ and $R^{54}$ are other than hydrogen, unsubstituted or hydroxy-substituted $C_1$–$C_6$-alkyl, halogen, amino, $C_1$–$C_6$-alkylamino or di($C_1$–$C_6$-alkyl)amino and $R^{55}$ is other than unsubstituted or substituted phenyl, thienyl, furyl, pyrrolyl or oxazolyl;

and provided that the compound of formula I is other than N-(2-amino-5,6,7,8-tetrahydro-4-hydroxyquinazolin-6-yl)-3,4-dichlorobenzamide.

2. A compound according to claim 1 wherein the ring A is an aromatic 6-membered ring containing 1 or 2 nitrogen atoms as ring heteroatoms.

3. A compound according to claim 1 wherein the ring A is an aromatic 5-membered ring containing a sulfur atom as ring heteroatom or a sulfur atom and a nitrogen atom as ring heteroatoms.

4. A compound according to claim 1 wherein n is 1.

5. A compound according to claim 1 wherein n is 3.

6. A compound according to claim 1, wherein $R^1$ and $R^4$ are independently from one another selected from the group consisting of H, $C_1$–$C_4$-alkyl and halogen and the residues $R^2$ and $R^3$ are independently from one another selected from the group consisting of H, $C_1$–$C_4$-alkyl and halogen.

7. A pharmaceutical preparation, comprising an pharmaceutically effective amount of a compound according to claim 1 and a pharmaceutically acceptable carrier.

8. A method for the stimulation of the expression of endothelial NO synthase to treat a disease selected from the group consisting of cardiovascular disease, stroke, endothelial dysfunction, atherosclerosis hypertension, diabetes and angiogenesis, in a patient in need thereof, comprising administering to such patient a pharmaceutically effective amount of a compound of the formula I,

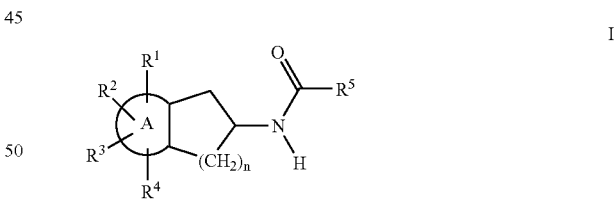

wherein:

the ring A, which comprises the two carbon atoms common to the ring A and the cycloalkenyl ring in formula I, is an aromatic 5-membered or 6-membered ring containing 1 or 2 nitrogen atoms as ring heteroatoms, or ring A is an aromatic 5-membered ring containing 1 ring heteroatom which is an oxygen atom or a sulfur atom or containing 2 ring heteroatoms one of which is a nitrogen atom and the other of which is an oxygen atom or a sulfur atom;

$R^1$ and $R^4$ are independently from each other:

H;

unsubstituted or substituted $C_1$–$C_{10}$-alkyl, unsubstituted or substituted $C_2$–$C_{10}$-alkenyl or unsubstituted or substituted $C_2$–$C_{10}$-alkynyl, the substituents of which are selected from the group consisting of F, OH, $C_1$–$C_8$-alkoxy, $C_1$–$C_8$-alkylmercapto, —CN, COOR$^6$, CONR$^7$R$^8$, and unsubstituted or substituted phenyl or unsubstituted or substituted heteroaryl where the substituents of the phenyl and heteroaryl group are selected from the group consisting of halogen, —CN, $C_1$–$C_3$-alkyl, $C_1$–$C_3$-alkoxy and CF$_3$;

unsubstituted or substituted phenyl or heteroaryl the substituents of which are selected from the group consisting of halogen, —CN, $C_1$–$C_3$-alkyl, $C_1$–$C_3$-alkoxy and CF$_3$;

COR$^9$; CONR$^{10}$R$^{11}$; COOR$^{12}$; CF$_3$; halogen; —CN; NR$^{13}$R$^{14}$; OR$^{15}$; S(O)$_m$R$^{16}$; SO$_2$NR$^{17}$R$^{18}$; or NO$_2$;

provided that, when R$^1$ or R$^4$, in each case, is bonded to a ring nitrogen atom, then R$^1$ or R$^4$, in each case, is other than halogen, —CN or NO$_2$;

R$^2$ and R$^3$ are independently from each other:

H; halogen;

unsubstituted or substituted $C_1$–$C_{10}$-alkyl the substituents of which are selected from the group consisting of OH, phenyl, and heteroaryl;

OH; $C_1$–$C_{10}$-alkoxy; phenoxy; S(O)$_m$R$^{19}$; CF$_3$; —CN; NO$_2$; $C_1$–$C_{10}$-alkylamino; di($C_1$–$C_{10}$-alkyl)amino; ($C_1$–$C_6$-alkyl)—CONH—;

unsubstituted or substituted phenyl-CONH— or unsubstituted or substituted phenyl-SO$_2$—O— the substituents of which are selected from the group consisting of halogen, —CN, methyl and methoxy;

$C_1$–$C_6$-alkyl-SO$_2$—O—;

unsubstituted or substituted ($C_1$–$C_6$-alkyl)—CO— the substituents of which are selected from the group consisting of F, di($C_1$–$C_3$-alkyl)amino, pyrrolidinyl and piperidinyl; or phenyl-CO— the phenyl part of which is unsubstituted or substituted by substituents selected from the group consisting of $C_1$–$C_3$-alkyl, halogen and methoxy;

provided that, when R$^2$ or R$^3$, in each case, is bonded to a ring nitrogen atom, then R$^2$ or R$^3$, in each case, is other than halogen, —CN or NO$_2$;

provided that, when A is a 6-membered aromatic ring, then two or three of the groups R$^1$, R$^2$, R$^3$ and R$^4$ are present and are bonded to the carbon atoms in the ring A which are not shared with the cycloalkenyl ring of formula I, and provided that when A is a 5-membered aromatic ring, then one, two or three of the groups R$^1$, R$^2$, R$^3$ and R$^4$ are present and are bonded to the carbon atoms in the ring A which are not shared with the cycloalkenyl ring of formula I, and, when ring A is a pyrrole, pyrazole or imidazole ring, to one ring nitrogen;

R$^5$ is a group Ar or a group Hetar each of which is unsubstituted or carries one or more identical or different substituents selected from the group consisting of:

halogen; —CN; NH$_2$;

unsubstituted or substituted $C_1$–$C_{10}$-alkyl, unsubstituted or substituted $C_2$–$C_{10}$-alkenyl, unsubstituted or substituted $C_2$–$C_{10}$-alkynyl, unsubstituted or substituted $C_1$–$C_{10}$-alkoxy, unsubstituted or substituted $C_1$–$C_{10}$-alkylamino and unsubstituted or substituted di($C_1$–$C_{10}$-alkyl)amino, the substituents of each of which are selected from the group consisting of F, OH, $C_1$–$C_8$-alkoxy, aryloxy, $C_1$–$C_8$-alkylmercapto, NH$_2$, $C_1$–$C_8$-alkylamino and di($C_1$–$C_8$-alkyl)amino;

$C_3$–$C_5$-alkandiyl; phenyl; heteroaryl; aryl-substituted or heteroaryl-substituted $C_1$–$C_4$-alkyl; CF$_3$; NO$_2$; OH; phenoxy; benzyloxy; ($C_1$–$C_{10}$-alkyl)—COO—; S(O)$_m$R$^{20}$; SH; phenylamino; benzylamino; ($C_1$–$C_{10}$-alkyl)—CONH—; ($C_1$–$C_{10}$-alkyl)—CO—N($C_1$–$C_4$-alkyl)—; phenyl-CONH—; phenyl-CO—N($C_1$–$C_4$-alkyl)—; heteroaryl-CONH—; heteroaryl-CO—N($C_1$–$C_4$-alkyl)—; ($C_1$–$C_{10}$-alkyl)—CO—; phenyl-CO—; heteroaryl-CO—; CF$_3$—CO—; —OCH$_2$O—; —OCF$_2$O—; —OCH$_2$CH$_2$O—; —CH$_2$CH$_2$O—; COOR$^{21}$; CONR$^{22}$R$^{23}$; C(NH)—NH$_2$; SO$_2$NR$^{24}$R$^{25}$; R$^{26}$SO$_2$NH—; R$^{27}$SO$_2$N($C_1$–$C_6$-alkyl)—; or a residue of a saturated or at least monounsaturated aliphatic, monocyclic 5-membered to 7-membered heterocycle containing 1, 2 or 3 heteroatoms selected from the group consisting of N, O and S, which heterocycle can be substituted by one or more substituents selected from the group consisting of halogen, $C_1$–$C_3$-alkyl, $C_1$–$C_3$-alkoxy, OH, oxo and CF$_3$, where said heterocycle can optionally be condensed to the said group Ar or the said group Hetar;

wherein all aryl, heteroaryl, phenyl, aryl-containing, heteroaryl-containing and phenyl-containing groups, which are optionally present in the said substituents of the said group Ar or the said group Hetar, can be substituted by one or more substituents selected from the group consisting of halogen, —CN, $C_1$–$C_3$-alkyl, OH, $C_1$–$C_3$-alkoxy, and CF$_3$;

R$^6$ is

H;

$C_1$–$C_{10}$-alkyl which can be substituted by one or more substituents selected from the group consisting of F, $C_1$–$C_8$-alkoxy and di($C_1$–$C_8$-alkyl)amino;

aryl-($C_1$–$C_4$-alkyl)— or heteroaryl-($C_1$–$C_4$-alkyl)— each of which can be substituted by one or more substituents selected from the group consisting of halogen, $C_1$–$C_4$-alkyl, $C_1$–$C_4$-alkoxy and di($C_1$–$C_6$-alkyl)amino;

R$^7$ is

H;

$C_1$–$C_{10}$-alkyl which can be substituted by one or more substituents selected from the group consisting of F, $C_1$–$C_8$-alkoxy, di($C_1$–$C_8$-alkyl)amino and phenyl;

phenyl; indanyl; or heteroaryl;

wherein each of the aromatic groups can be unsubstituted or carry one or more substituents selected from the group consisting of halogen, —CN, $C_1$–$C_3$-alkyl, $C_1$–$C_3$-alkoxy and CF$_3$;

R$^8$ is H or $C_1$–$C_{10}$-alkyl;

R$^9$ is $C_1$–$C_{10}$-alkyl which can be substituted by one or more substituents selected from the group consisting of F, $C_1$–$C_4$-alkoxy and di($C_1$–$C_3$-alkyl)amino; or unsubstituted or substituted phenyl or unsubstituted or substituted heteroaryl the substituents of each of which are selected from the group consisting of $C_1$–$C_3$-alkyl, $C_1$–$C_3$-alkoxy, halogen, —CN and CF$_3$;

R$^{10}$, independently from R$^7$, is R$^7$;

R$^{11}$, independently from R$^8$, is R$^8$;

R$^{12}$, independently from R$^6$, is R$^6$;

R$^{13}$ is

H; $C_1$–$C_6$-alkyl;

unsubstituted or substituted phenyl, unsubstituted or substituted benzyl, unsubstituted or substituted heteroaryl, unsubstituted or substituted ($C_1$–$C_6$-alkyl)—CO—, unsubstituted or substituted phenyl-CO—, or unsubstituted or substituted heteroaryl-CO—, the substituents of each of which are selected from the group consisting of halogen, —CN, $C_1$–$C_3$-alkyl, $C_1$–$C_3$-alkoxy and $CF_3$, wherein one or more of these substituents can be present;

$R^{14}$, independently from $R^{13}$, is $R^{13}$;

$R^{15}$ is

H; $C_1$–$C_{10}$-alkyl; ($C_1$–$C_3$-alkoxy)—$C_1$–$C_3$-alkyl-; or substituted or unsubstituted benzyl, substituted or unsubstituted phenyl or substituted or unsubstituted heteroaryl, the substituents of each of which are selected from the group consisting of halogen, —CN, $C_1$–$C_3$-alkyl, $C_1$–$C_3$-alkoxy and $CF_3$, wherein one or more of these substituents can be present;

$R^{16}$ is $C_1$–$C_{10}$-alkyl which can be substituted by one or more substituents selected from the group consisting of F, OH, $C_1$–$C_8$-alkoxy, aryloxy, $C_1$–$C_8$-alkylmercapto, $C_1$–$C_8$-alkylamino and di($C_1$–$C_8$-alkyl)amino;

$CF_3$; or substituted or unsubstituted phenyl or substituted or unsubstituted heteroaryl, the substituents of which are selected from the group consisting of halogen, —CN, $C_1$–$C_3$-alkyl, $C_1$–$C_3$-alkoxy and $CF_3$, wherein one or more of these substituents can be present;

$R^{17}$, independently from $R^7$, is $R^7$;
$R^{18}$, independently from $R^8$, is $R^8$;
$R^{19}$, independently from $R^{16}$, is $R^{16}$;
$R^{20}$, independently from $R^{16}$, is $R^{16}$;
$R^{21}$, independently from $R^6$, is $R^6$;
$R^{22}$, independently from $R^7$, is $R^7$;
$R^{23}$, independently from $R^8$, is $R^8$;
$R^{24}$, independently from $R^7$, is $R^7$;
$R^{25}$, independently from $R^8$, $R^8$;
$R^{26}$, independently from $R^{16}$, is $R^{16}$;
$R^{27}$, independently from $R^{16}$, is $R^{16}$;

heteroaryl is a residue of a 5-membered to 10-membered, aromatic, monocyclic or bicyclic heterocycle containing one or more heteroatoms selected from the group consisting of N, O and S;

the group Hetar is a residue of a 5-membered to 10-membered, aromatic, monocyclic or bicyclic heterocycle containing one or more heteroatoms selected from the group consisting of N, O and S;

aryl is phenyl, naphth-1-yl or naphth-2-yl;

the group Ar is phenyl, naphth-1-yl or naphth-2-yl;

m is 0, 1 or 2;

n is 1, 2 or 3; or a stereoisomer or a mixture of stereoisomers of such compound in any ratio, or a pharmaceutically acceptable salt of such compound, stereoisomer or mixture.

9. A method for the treatment of cardiovascular disease, stroke, endothelial dysfunction, atherosclerosis, hypertension, angiogenesis, in a patient in need thereof, comprising administering to such patient a pharmaceutically effective amount of a compound of the formula I

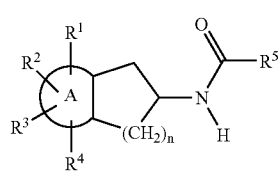

I wherein:

the ring A, which comprises the two carbon atoms common to the ring A and the cycloalkenyl ring in formula I, is an aromatic 5-membered or 6-membered ring containing 1 or 2 nitrogen atoms as ring heteroatoms, or ring A is an aromatic 5-membered ring containing 1 ring heteroatom which is an oxygen atom or a sulfur atom or containing 2 ring heteroatoms one of which is a nitrogen atom and the other of which is an oxygen atom or a sulfur atom;

$R^1$ and $R^4$ are independently from each other:

H;

unsubstituted or substituted $C_1$–$C_{10}$-alkyl, unsubstituted or substituted $C_2$–$C_{10}$-alkenyl or unsubstituted or substituted $C_2$–$C_{10}$-alkynyl, the substituents of which are selected from the group consisting of F, OH, $C_1$–$C_8$-alkoxy, $C_1$–$C_8$-alkylmercapto, —CN, $COOR^6$, $CONR^7R^8$, and unsubstituted or substituted phenyl or unsubstituted or substituted heteroaryl where the substituents of the phenyl and heteroaryl group are selected from the group consisting of halogen, —CN, $C_1$–$C_3$-alkyl, $C_1$–$C_3$-alkoxy and $CF_3$;

unsubstituted or substituted phenyl or heteroaryl the substituents of which are selected from the group consisting of halogen, —CN, $C_1$–$C_3$-alkyl, $C_1$–$C_3$-alkoxy and $CF_3$;

$COR^9$; $CONR^{10}R^{11}$; $COOR^{12}$; $CF_3$; halogen; —CN; $NR^{13}R^{14}$; $OR^{15}$; $S(O)_mR^{16}$; $SO_2NR^{17}R^{18}$; or $NO_2$;

provided that, when $R^1$ or $R^4$, in each case, is bonded to a ring nitrogen atom, then $R^1$ or $R^4$, in each case, is other than halogen, —CN or $NO_2$;

$R^2$ and $R^3$ are independently from each other:

H; halogen;

unsubstituted or substituted $C_1$–$C_{10}$-alkyl the substituents of which are selected from the group consisting of OH, phenyl, and heteroaryl;

OH; $C_1$–$C_{10}$-alkoxy; phenoxy; $S(O)_mR^{19}$; $CF_3$; —CN; $NO_2$; $C_1$–$C_{10}$-alkylamino; di($C_1$–$C_{10}$-alkyl)amino; ($C_1$–$C_6$-alkyl)—CONH—;

unsubstituted or substituted phenyl-CONH— or unsubstituted or substituted phenyl-$SO_2$—O— the substituents of which are selected from the group consisting of halogen, —CN, methyl and methoxy;

$C_1$–$C_6$-alkyl-$SO_2$—O—;

unsubstituted or substituted ($C_1$–$C_6$-alkyl)—CO— the substituents of which are selected from the group consisting of F, di($C_1$–$C_3$-alkyl)amino, pyrrolidinyl and piperidinyl; or phenyl-CO— the phenyl part of which is unsubstituted or substituted by substituents selected from the group consisting of $C_1$–$C_3$-alkyl, halogen and methoxy;

provided that, when $R^2$ or $R^3$, in each case, is bonded to a ring nitrogen atom, then $R^2$ or $R^3$, in each case, is other than halogen, —CN or $NO_2$;

provided that, when A is a 6-membered aromatic ring, then two or three of the groups $R^1$, $R^2$, $R^3$ and $R^4$ are present and are bonded to the carbon atoms in the ring A which are not shared with the cycloalkenyl ring of formula I, and provided that when A is a 5-membered aromatic ring, then one, two or three of the groups $R^1$, $R^2$, $R^3$ and $R^4$ are present and are bonded to the carbon atoms in the ring A which are not shared with the cycloalkenyl ring of formula I, and, when ring A is a pyrrole, pyrazole or imidazole ring, to one ring nitrogen;

$R^5$ is a group Ar or a group Hetar each of which is unsubstituted or carries one or more identical or different substituents selected from the group consisting of:

halogen; —CN; $NH_2$;

unsubstituted or substituted $C_1$–$C_{10}$-alkyl, unsubstituted or substituted $C_2$–$C_{10}$-alkenyl, unsubstituted or substituted $C_2$–$C_{10}$-alkynyl, unsubstituted or substituted $C_1$–$C_{10}$-alkoxy, unsubstituted or substituted $C_1$–$C_{10}$-alkylamino and unsubstituted or substituted di($C_1$–$C_{10}$-alkyl)amino, the substituents of each of which are selected from the group consisting of F, OH, $C_1$–$C_8$-alkoxy, aryloxy, $C_1$–$C_8$-alkylmercapto, $NH_2$, $C_1$–$C_8$-alkylamino and di($C_1$–$C_8$-alkyl)amino;

$C_3$–$C_5$-alkandiyl; phenyl; heteroaryl; aryl-substituted or heteroaryl-substituted $C_1$–$C_4$-alkyl; $CF_3$; $NO_2$; OH; phenoxy; benzyloxy; ($C_1$–$C_{10}$-alkyl)—COO—; $S(O)_m R^{20}$; SH; phenylamino; benzylamino; ($C_1$–$C_{10}$-alkyl)—CONH—; ($C_1$–$C_{10}$-alkyl)—CO—N($C_1$–$C_4$-alkyl)—; phenyl-CONH—; phenyl-CO—N($C_1$–$C_4$-alkyl)—; heteroaryl-CONH—; heteroaryl-CO—N($C_1$–$C_4$-alkyl)—; ($C_1$–$C_{10}$-alkyl)—CO—; phenyl-CO—; heteroaryl-CO—; $CF_3$—CO—; —$OCH_2O$—; —$OCF_2O$—; —$OCH_2CH_2O$—; —$CH_2CH_2O$—; $COOR^{21}$; $CONR^{22}R^{23}$; C(NH)—$NH_2$; $SO_2NR^{24}R^{25}$; $R^{26}SO_2NH$—; $R^{27}SO_2N(C_1$–$C_6$-alkyl)—; or a residue of a saturated or at least monounsaturated aliphatic, monocyclic 5-membered to 7-membered heterocycle containing 1, 2 or 3 heteroatoms selected from the group consisting of N, O and S, which heterocycle can be substituted by one or more substituents selected from the group consisting of halogen, $C_1$–$C_3$-alkyl, $C_1$–$C_3$-alkoxy, OH, oxo and $CF_3$, where said heterocycle can optionally be condensed to the said group Ar or the said group Hetar;

wherein all aryl, heteroaryl, phenyl, aryl-containing, heteroaryl-containing and phenyl-containing groups, which are optionally present in the said substituents of the said group Ar or the said group Hetar, can be substituted by one or more substituents selected from the group consisting of halogen, —CN, $C_1$–$C_3$-alkyl, OH, $C_1$–$C_3$-alkoxy, and $CF_3$;

$R^6$ is

H;

$C_1$–$C_{10}$-alkyl which can be substituted by one or more substituents selected from the group consisting of F, $C_1$–$C_8$-alkoxy and di($C_1$–$C_8$-alkyl)amino;

aryl-($C_1$–$C_4$-alkyl)— or heteroaryl-($C_1$–$C_4$-alkyl)— each of which can be substituted by one or more substituents selected from the group consisting of halogen, $C_1$–$C_4$-alkyl, $C_1$–$C_4$-alkoxy and di($C_1$–$C_6$-alkyl)amino;

$R^7$ is

H;

$C_1$–$C_{10}$-alkyl which can be substituted by one or more substituents selected from the group consisting of F, $C_1$–$C_8$-alkoxy, di($C_1$–$C_8$-alkyl)amino and phenyl;

phenyl; indanyl; or heteroaryl;

wherein each of the aromatic groups can be unsubstituted or carry one or more substituents selected from the group consisting of halogen, —CN, $C_1$–$C_3$-alkyl, $C_1$–$C_3$-alkoxy and $CF_3$;

$R^8$ is H or $C_1$–$C_{10}$-alkyl;

$R^9$ is $C_1$–$C_{10}$-alkyl which can be substituted by one or more substituents selected from the group consisting of F, $C_1$–$C_4$-alkoxy and di($C_1$–$C_3$-alkyl)amino; or unsubstituted or substituted phenyl or unsubstituted or substituted heteroaryl the substituents of each of which are selected from the group consisting of $C_1$–$C_3$-alkyl, $C_1$–$C_3$-alkoxy, halogen, —CN and $CF_3$;

$R^{10}$, independently from $R^7$, is $R^7$;

$R^{11}$, independently from $R^8$, is $R^8$;

$R^{12}$, independently from $R^6$, is $R^6$;

$R^{13}$ is

H; $C_1$–$C_6$-alkyl;

unsubstituted or substituted phenyl, unsubstituted or substituted benzyl, unsubstituted or substituted heteroaryl, unsubstituted or substituted ($C_1$–$C_6$-alkyl)—CO—, unsubstituted or substituted phenyl-CO—, or unsubstituted or substituted heteroaryl-CO—, the substituents of each of which are selected from the group consisting of halogen, —CN, $C_1$–$C_3$-alkyl, $C_1$–$C_3$-alkoxy and $CF_3$, wherein one or more of these substituents can be present;

$R^{14}$, independently from $R^{13}$, is $R^{13}$;

$R^{15}$ is

H; $C_1$–$C_{10}$-alkyl; ($C_1$–$C_3$-alkoxy)—$C_1$–$C_3$-alkyl-; or substituted or unsubstituted benzyl, substituted or unsubstituted phenyl or substituted or unsubstituted heteroaryl, the substituents of each of which are selected from the group consisting of halogen, —CN, $C_1$–$C_3$-alkyl, $C_1$–$C_3$-alkoxy and $CF_3$, wherein one or more of these substituents can be present;

$R^{16}$ is $C_1$–$C_{10}$-alkyl which can be substituted by one or more substituents selected from the group consisting of F, OH, $C_1$–$C_8$-alkoxy, aryloxy, $C_1$–$C_8$-alkylmercapto, $C_1$–$C_8$-alkylamino and di($C_1$–$C_8$-alkyl)amino;

$CF_3$; or substituted or unsubstituted phenyl or substituted or unsubstituted heteroaryl, the substituents of which are selected from the group consisting of halogen, —CN, $C_1$–$C_3$-alkyl, $C_1$–$C_3$-alkoxy and $CF_3$, wherein one or more of these substituents can be present;

$R^{17}$, independently from $R^7$, is $R^7$;

$R_{18}$, independently from $R^8$, is $R^8$;

$R^{19}$, independently from $R^{16}$, is $R^{16}$;

$R^{20}$, independently from $R^{16}$, is $R^{16}$;

$R^{21}$, independently from $R^6$, is $R^6$;

$R^{22}$, independently from $R^7$, is $R^7$;

$R^{23}$, independently from $R^8$, is $R^8$;

$R^{24}$, independently from $R^7$, is $R^7$;

$R^{25}$, independently from $R^8$, $R^8$;

$R^{26}$, independently from $R^{16}$, is $R^{16}$;

$R^{27}$, independently from $R^{16}$, is $R^{16}$;

heteroaryl is a residue of a 5-membered to 10-membered, aromatic, monocyclic or bicyclic heterocycle containing one or more heteroatoms selected from the group consisting of N, O and S;

the group Hetar is a residue of a 5-membered to 10-membered, aromatic, monocyclic or bicyclic heterocycle containing one or more heteroatoms selected from the group consisting of N, O and S;

aryl is phenyl, naphth-1-yl or naphth-2-yl;

the group Ar is phenyl, naphth-1-yl or naphth-2-yl;

m is 0, 1 or 2;

n is 1, 2 or 3; or a stereoisomer or a mixture of stereoisomers of such compound in any ratio, or a pharmaceutically acceptable salt of such compound, stereoisomer or mixture.

* * * * *